United States Patent [19]

Sobel

[11] Patent Number: 5,780,021
[45] Date of Patent: Jul. 14, 1998

[54] METHOD FOR TREATING TYPE 1 DIABETES USING α-INTERFERON AND/OR β-INTERFERON

[75] Inventor: Douglas O. Sobel, Washington, D.C.

[73] Assignee: Georgetown University, Washington, D.C.

[21] Appl. No.: 26,758

[22] Filed: Mar. 5, 1993

[51] Int. Cl.$^6$ .................. A61K 38/19; C07K 14/555
[52] U.S. Cl. .................. 424/85.4; 424/85.6; 424/85.7; 435/69.51; 530/351; 514/2
[58] Field of Search .................. 514/2; 530/351; 424/85.6, 85.4, 85.7; 435/69.1, 69.51

[56] References Cited

U.S. PATENT DOCUMENTS 5,310,729  5/1994  Lernhardt .................. 514/5

OTHER PUBLICATIONS

Rehberg et al, J. Biol. Chem., 257, 11497–11502, 1982.
Becker et al., Clinical Immunology and Immunopathology, 56, 219–225, 1990.
Acceleration of Spontaneous Diabetes in the BB Rate by Poly I:C by Cynthia Hall Ewel, M.S., Washington, D.C., Nov. 22, 1988.
Fudenberg, H. Hugh & McCluskey, Robert T., Clinical Immunology and Immunopathology, Academic Press, Inc., vol. 43, No. 3, 1987, pp. 362–371.
Archives of Neurology, vol. 43, No. 12, Dec. 1986, David L. Camenga, et al., pp. 1239–1246, "Systemic Recombinant Alpha 2 Interferon Therapy In Relapsing Multiple Sclerosis".
Rivsta di Neurologia, vol. 59, No. 5, Oct. 1989, Luca Durelli, et al., pp. 191–201, "Multiple Sclerosis. II. A Critical Assessment of Immunotherapy".
Proceedings of National Academy of Science, USA, vol. 80, pp. 3632–3636, Pravinkumar B. Sehgal, et al., "Isolation Of Novel Human Genomic DNA Clones Related To Human Interferon–Beta 1 cDNA", Jun. 1983.
Quarterly Journal of Medicine, New Series 54, No. 214, pp. 117–124, Tyrrell, "Interferons And The Physician", Feb. 1985.
Journal of Biological Regulators and Homeostatic Agents, vol. 3, No. 2, 1989, pp. 47–49, B.J. Boucher, et al., "Estimates Of Normal Binding Of A Human Recombinant Alpha Interferon To Peripheral Blood Mononuclear Cells From A Study Matching Healthy Subjects To Subjects With Insulin Dependent Diabetes".
Durelli et al., Riv. Neurol., 59, 191–201, 1989.

*Primary Examiner*—Sally P. Teng
*Attorney, Agent, or Firm*—Burns, Doane, Swecker & Mathis, LLP

[57] ABSTRACT

A method is provided for preventing or treating an autoimmune disorder and/or recurrent autoimmune disorder in a transplant tissue in a mammal, which entails administering an effective amount of a single subtype of α- and/or β-interferon or a hybrid or analog of either or mixture thereof to the mammal.

24 Claims, 2 Drawing Sheets

EFFECT OF A-IFN TREATMENT ON THE DEVELOPMENT OF DIABETES

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
        ( A ) LENGTH: 189 amino acids
        ( B ) TYPE: amino acid
        ( D ) TOPOLOGY: unknown ( i i ) MOLECULE TYPE: protein ( i x ) FEATURE:
        ( A ) NAME/KEY: Protein
        ( B ) LOCATION: 24..189
        ( D ) OTHER INFORMATION: /note= "IFN-alpha consensus"

( i x ) FEATURE:
        ( A ) NAME/KEY: Modified-site
        ( B ) LOCATION: 55
        ( D ) OTHER INFORMATION: /note= "The one-letter code at position 55 appears to be a typographical error in Table 1 of the specification."

( i x ) FEATURE:
        ( A ) NAME/KEY: Modified-site
        ( B ) LOCATION: 124
        ( D ) OTHER INFORMATION: /note= "The one-letter code at position 124 appears to be a typographical error in Table 1 of the specification."

( x i ) SEQUENCE DESCRIPTION: SEQ ID NO:1:

```
Met  Ala  Leu  Ser  Phe  Ser  Leu  Leu  Met  Ala  Val  Leu  Val  Leu  Ser  Tyr
          -20                      -15                      -10

Lys  Ser  Ile  Cys  Ser  Leu  Gly  Cys  Asp  Leu  Pro  Gln  Thr  His  Ser  Leu
          -5                       1                        5

Gly  Asn  Arg  Arg  Ala  Leu  Ile  Leu  Leu  Ala  Gln  Met  Gly  Arg  Ile  Ser
10                       15                      20                       25

Pro  Phe  Ser  Cys  Leu  Lys  Xaa  Arg  His  Asp  Phe  Gly  Phe  Pro  Gln  Glu
                    30                       35                      40

Glu  Phe  Asp  Gly  Asn  Gln  Phe  Gln  Lys  Ala  Gln  Ala  Ile  Ser  Val  Leu
               45                       50                       55

His  Glu  Met  Ile  Gln  Gln  Thr  Phe  Asn  Leu  Phe  Ser  Thr  Lys  Asp  Ser
          60                       65                      70

Ser  Ala  Ala  Trp  Asp  Glu  Ser  Leu  Leu  Glu  Lys  Phe  Ser  Thr  Glu  Leu
     75                       80                      85

Tyr  Gln  Gln  Leu  Asn  Asp  Leu  Glu  Ala  Cys  Val  Xaa  Gln  Glu  Val  Gly
90                       95                      100                      105

Val  Glu  Glu  Thr  Pro  Leu  Met  Asn  Glu  Asp  Ser  Ile  Leu  Ala  Val  Arg
               110                      115                      120

Lys  Tyr  Phe  Gln  Arg  Ile  Thr  Leu  Tyr  Leu  Thr  Glu  Lys  Lys  Tyr  Ser
               125                      130                      135

Pro  Cys  Ala  Trp  Glu  Val  Val  Arg  Ala  Glu  Ile  Met  Arg  Ser  Phe  Ser
               140                      145                      150

Phe  Ser  Thr  Asn  Leu  Gln  Lys  Arg  Leu  Arg  Arg  Lys  Asp
     155                      160                      165
```

( 2 ) INFORMATION FOR SEQ ID NO:2:

( i ) SEQUENCE CHARACTERISTICS:
        ( A ) LENGTH: 189 amino acids
        ( B ) TYPE: amino acid
        ( D ) TOPOLOGY: unknown ( i i ) MOLECULE TYPE: protein ( i x ) FEATURE:
        ( A ) NAME/KEY: Protein
        ( B ) LOCATION: 24..189
        ( D ) OTHER INFORMATION: /note= "IFN-alpha-1"

( x i ) SEQUENCE DESCRIPTION: SEQ ID NO:2:

```
Met  Ala  Ser  Pro  Phe  Ala  Leu  Leu  Met  Val  Leu  Val  Val  Leu  Ser  Cys
          -20                      -15                      -10

Lys  Ser  Ser  Cys  Ser  Leu  Gly  Cys  Asp  Leu  Pro  Glu  Thr  His  Ser  Leu
          -5                       1                        5

Asp  Asn  Arg  Arg  Thr  Leu  Met  Leu  Leu  Ala  Gln  Met  Ser  Arg  Ile  Ser
10                       15                      20                       25

Pro  Ser  Ser  Cys  Leu  Met  Xaa  Arg  His  Asp  Phe  Gly  Phe  Pro  Gln  Glu
                    30                       35                      40

Glu  Phe  Asp  Gly  Asn  Gln  Phe  Gln  Lys  Ala  Pro  Ala  Ile  Ser  Val  Leu
               45                       50                       55

His  Glu  Leu  Ile  Gln  Gln  Ile  Phe  Asn  Leu  Phe  Thr  Thr  Lys  Asp  Ser
          60                       65                      70

Ser  Ala  Ala  Trp  Asp  Glu  Asp  Leu  Leu  Asp  Lys  Phe  Cys  Thr  Glu  Leu
     75                       80                      85

Tyr  Gln  Gln  Leu  Asn  Asp  Leu  Glu  Ala  Cys  Val  Met  Gln  Glu  Glu  Arg
90                       95                      100                      105

Val  Gly  Glu  Thr  Pro  Leu  Met  Asn  Ala  Asp  Ser  Ile  Leu  Ala  Val  Lys
```

|     |     |     | 110 |     |     |     | 115 |     |     |     | 120 |     |     |
|-----|-----|-----|-----|-----|-----|-----|-----|-----|-----|-----|-----|-----|-----|
| Lys | Tyr | Phe | Arg | Arg | Ile | Thr | Leu | Tyr | Leu | Thr | Glu | Lys | Lys | Tyr | Ser |
|     |     |     | 125 |     |     |     | 130 |     |     |     |     | 135 |     |

Pro Cys Ala Trp Glu Val Val Arg Ala Glu Ile Met Arg Ser Leu Ser
        140             145             150

Leu Ser Thr Asn Leu Gln Glu Arg Leu Arg Arg Lys Glu
    155             160             165

(2) INFORMATION FOR SEQ ID NO:3:

(i) SEQUENCE CHARACTERISTICS:
     (A) LENGTH: 189 amino acids
     (B) TYPE: amino acid
     (D) TOPOLOGY: unknown (ii) MOLECULE TYPE: protein (ix) FEATURE:
     (A) NAME/KEY: Protein
     (B) LOCATION: 24..189
     (D) OTHER INFORMATION: /note= "IFN-alpha-D"

(xi) SEQUENCE DESCRIPTION: SEQ ID NO:3:

Met Ala Ser Pro Phe Ala Leu Leu Met Val Leu Val Val Leu Ser Cys
            -20                 -15                 -10

Lys Ser Ser Cys Ser Leu Gly Cys Asp Leu Pro Glu Thr His Ser Leu
        -5                   1                   5

Asp Asn Arg Arg Thr Leu Met Leu Leu Ala Gln Met Ser Arg Ile Ser
10                  15                  20                   25

Pro Ser Ser Cys Leu Met Xaa Arg His Asp Phe Gly Phe Pro Gln Glu
                30                  35                  40

Glu Phe Asp Gly Asn Gln Phe Gln Lys Ala Pro Ala Ile Ser Val Leu
            45                  50                  55

His Glu Leu Ile Gln Gln Ile Phe Asn Leu Phe Thr Thr Lys Asp Ser
        60                  65                  70

Ser Ala Ala Trp Asp Glu Asp Leu Leu Asp Lys Phe Cys Thr Glu Leu
75                  80                  85

Tyr Gln Gln Leu Asn Asp Leu Glu Ala Cys Val Met Gln Glu Glu Arg
90                  95                  100                 105

Val Gly Glu Thr Pro Leu Met Asn Val Asp Ser Ile Leu Ala Val Lys
                110                 115                 120

Lys Tyr Phe Arg Arg Ile Thr Leu Tyr Leu Thr Glu Lys Lys Tyr Ser
        125                 130                         135

Pro Cys Ala Trp Glu Val Val Arg Ala Glu Ile Met Arg Ser Leu Ser
        140             145             150

Leu Ser Thr Asn Leu Gln Glu Arg Leu Arg Arg Lys Glu
    155             160             165

(2) INFORMATION FOR SEQ ID NO:4:

(i) SEQUENCE CHARACTERISTICS:
     (A) LENGTH: 189 amino acids
     (B) TYPE: amino acid
     (D) TOPOLOGY: unknown (ii) MOLECULE TYPE: protein (ix) FEATURE:
     (A) NAME/KEY: Protein
     (B) LOCATION: 24..189
     (D) OTHER INFORMATION: /note= "IFN-alpha-2"

(xi) SEQUENCE DESCRIPTION: SEQ ID NO:4:

```
Met  Ala  Leu  Thr  Phe  Ala  Leu  Leu  Val  Ala  Leu  Leu  Val  Leu  Ser  Cys
          -20                      -15                     -10

Lys  Ser  Ser  Cys  Ser  Val  Gly  Cys  Asp  Leu  Pro  Gln  Thr  His  Ser  Leu
           -5                 1                      5

Gly  Ser  Arg  Arg  Thr  Leu  Met  Leu  Leu  Ala  Gln  Met  Arg  Arg  Ile  Ser
 10                       15                      20                         25

Leu  Phe  Ser  Cys  Leu  Lys  Xaa  Arg  His  Asp  Phe  Gly  Phe  Pro  Gln  Glu
                30                      35                          40

Glu  Phe  Asp  Gly  Asn  Gln  Phe  Gln  Lys  Ala  Glu  Thr  Ile  Pro  Val  Leu
               45                      50                          55

His  Glu  Met  Ile  Gln  Gln  Ile  Phe  Asn  Leu  Phe  Ser  Thr  Lys  Asp  Ser
          60                       65                     70

Ser  Ala  Ala  Trp  Asp  Glu  Thr  Leu  Leu  Asp  Lys  Phe  Tyr  Thr  Glu  Leu
     75                      80                       85

Tyr  Gln  Gln  Leu  Asn  Asp  Leu  Glu  Ala  Cys  Val  Xaa  Gln  Gly  Val  Gly
 90                      95                      100                        105

Val  Thr  Glu  Thr  Pro  Leu  Met  Lys  Glu  Asp  Ser  Ile  Leu  Ala  Val  Arg
                110                      115                         120

Lys  Tyr  Phe  Gln  Arg  Ile  Thr  Leu  Tyr  Leu  Lys  Glu  Lys  Lys  Tyr  Ser
               125                      130                         135

Pro  Cys  Ala  Trp  Glu  Val  Val  Arg  Ala  Glu  Ile  Met  Arg  Ser  Phe  Ser
               140                      145                    150

Leu  Ser  Thr  Asn  Leu  Gln  Glu  Ser  Leu  Arg  Ser  Lys  Glu
 155                     160                     165
```

( 2 ) INFORMATION FOR SEQ ID NO:5:

( i ) SEQUENCE CHARACTERISTICS:
        ( A ) LENGTH: 189 amino acids
        ( B ) TYPE: amino acid
        ( D ) TOPOLOGY: unknown ( i i ) MOLECULE TYPE: protein ( i x ) FEATURE:
        ( A ) NAME/KEY: Protein
        ( B ) LOCATION: 24..189
        ( D ) OTHER INFORMATION: /note= "IFN-alpha-A"

( x i ) SEQUENCE DESCRIPTION: SEQ ID NO:5:

```
Met  Ala  Leu  Thr  Phe  Ala  Leu  Leu  Val  Ala  Leu  Leu  Val  Leu  Ser  Cys
          -20                      -15                     -10

Lys  Ser  Ser  Cys  Ser  Val  Gly  Cys  Asp  Leu  Pro  Gln  Thr  His  Ser  Leu
           -5                 1                      5

Gly  Ser  Arg  Arg  Thr  Leu  Met  Leu  Leu  Ala  Gln  Met  Arg  Lys  Ile  Ser
 10                       15                      20                         25

Leu  Phe  Ser  Cys  Leu  Lys  Xaa  Arg  His  Asp  Phe  Gly  Phe  Pro  Gln  Glu
                30                      35                          40

Glu  Phe  Asp  Gly  Asn  Gln  Phe  Gln  Lys  Ala  Glu  Thr  Ile  Pro  Val  Leu
               45                      50                          55

His  Glu  Met  Ile  Gln  Gln  Ile  Phe  Asn  Leu  Phe  Ser  Thr  Lys  Asp  Ser
          60                       65                     70

Ser  Ala  Ala  Trp  Asp  Glu  Thr  Leu  Leu  Asp  Lys  Phe  Tyr  Thr  Glu  Leu
     75                      80                       85

Tyr  Gln  Gln  Leu  Asn  Asp  Leu  Glu  Ala  Cys  Val  Xaa  Gln  Gly  Val  Gly
 90                      95                      100                        105

Val  Thr  Glu  Thr  Pro  Leu  Met  Lys  Glu  Asp  Ser  Ile  Leu  Ala  Val  Arg
                110                      115                         120
```

Lys Tyr Phe Gln Arg Ile Thr Leu Tyr Leu Lys Glu Lys Lys Tyr Ser
                    125                 130                 135

Pro Cys Ala Trp Glu Val Val Arg Ala Glu Ile Met Arg Ser Phe Ser
                    140                 145                 150

Leu Ser Thr Asn Leu Gln Glu Ser Leu Arg Ser Lys Glu
                    155                 160                 165

( 2 ) INFORMATION FOR SEQ ID NO:6:

( i ) SEQUENCE CHARACTERISTICS:
        ( A ) LENGTH: 189 amino acids
        ( B ) TYPE: amino acid
        ( D ) TOPOLOGY: unknown ( i i ) MOLECULE TYPE: protein ( i x ) FEATURE:
        ( A ) NAME/KEY: Protein
        ( B ) LOCATION: 24..189
        ( D ) OTHER INFORMATION: /note= "IFN-alpha-K (alpha-6)"

( x i ) SEQUENCE DESCRIPTION: SEQ ID NO:6:

Met Ala Leu Pro Phe Ala Leu Leu Met Ala Leu Val Val Leu Ser Cys
                    -20                 -15                 -10

Lys Ser Ser Cys Ser Leu Asp Cys Asp Leu Pro Gln Thr His Ser Leu
                    -5              1               5

Gly His Arg Arg Thr Met Met Leu Leu Ala Gln Met Arg Arg Ile Ser
        10                  15                  20                  25

Leu Phe Ser Cys Leu Lys Xaa Arg His Asp Phe Arg Phe Pro Gln Glu
                        30                  35                  40

Glu Phe Asp Gly Asn Gln Phe Gln Lys Ala Glu Ala Ile Ser Val Leu
                    45                  50                  55

His Glu Val Ile Gln Gln Thr Phe Asn Leu Phe Ser Thr Lys Asp Ser
                    60                  65                  70

Ser Val Ala Trp Asp Glu Arg Leu Leu Asp Lys Leu Tyr Thr Glu Leu
            75                  80                  85

Tyr Gln Gln Leu Asn Asp Leu Glu Ala Cys Val Met Gln Glu Val Trp
        90                  95                  100                 105

Val Gly Gly Thr Pro Leu Met Asn Glu Asp Ser Ile Leu Ala Val Arg
                        110                 115                 120

Lys Tyr Phe Gln Arg Ile Thr Leu Tyr Leu Thr Glu Lys Lys Tyr Ser
                    125                 130                 135

Pro Cys Ala Trp Glu Val Val Arg Ala Glu Ile Met Arg Ser Phe Ser
                    140                 145                 150

Ser Ser Arg Asn Leu Gln Glu Arg Leu Arg Arg Lys Glu
                    155                 160                 165

( 2 ) INFORMATION FOR SEQ ID NO:7:

( i ) SEQUENCE CHARACTERISTICS:
        ( A ) LENGTH: 189 amino acids
        ( B ) TYPE: amino acid
        ( D ) TOPOLOGY: unknown ( i i ) MOLECULE TYPE: protein ( i x ) FEATURE:
        ( A ) NAME/KEY: Protein
        ( B ) LOCATION: 24..189
        ( D ) OTHER INFORMATION: /note= "IFN-alpha-5(G)"

( x i ) SEQUENCE DESCRIPTION: SEQ ID NO:7:

-continued

| | | | | | | | | | | | | | |
|---|---|---|---|---|---|---|---|---|---|---|---|---|---|
| Met | Ala | Leu | Pro -20 | Phe | Val | Leu | Leu | Met -15 | Ala | Leu | Val | Val | Leu -10 | Asn | Cys |
| Lys | Ser | Ile -5 | Cys | Ser | Leu | Gly | Cys 1 | Asp | Leu | Pro | Gln 5 | Thr | His | Ser | Leu |
| Ser 10 | Asn | Arg | Arg | Thr | Leu 15 | Met | Ile | Met | Ala | Gln 20 | Met | Gly | Arg | Ile | Ser 25 |
| Pro | Phe | Ser | Cys | Leu 30 | Lys | Xaa | Arg | His | Asp 35 | Phe | Gly | Phe | Pro | Gln 40 | Glu |
| Glu | Phe | Asp | Gly 45 | Asn | Gln | Phe | Gln | Lys 50 | Ala | Gln | Ala | Ile | Ser 55 | Val | Leu |
| His | Glu | Met 60 | Ile | Gln | Gln | Thr | Phe 65 | Asn | Leu | Phe | Ser | Thr 70 | Lys | Asp | Ser |
| Ser | Ala 75 | Thr | Trp | Asp | Glu | Thr 80 | Leu | Leu | Asp | Lys | Phe 85 | Tyr | Thr | Glu | Leu |
| Tyr 90 | Gln | Gln | Leu | Asn | Asp 95 | Leu | Glu | Ala | Cys | Met 100 | Met | Gln | Glu | Val | Gly 105 |
| Val | Glu | Asp | Thr | Pro 110 | Leu | Met | Asn | Val | Asp 115 | Ser | Ile | Leu | Thr | Val 120 | Arg |
| Lys | Tyr | Phe | Gln 125 | Arg | Ile | Thr | Leu | Tyr 130 | Leu | Thr | Glu | Lys | Lys 135 | Tyr | Ser |
| Pro | Cys | Ala 140 | Trp | Glu | Val | Val | Arg 145 | Ala | Glu | Ile | Met | Arg 150 | Ser | Phe | Ser |
| Leu | Ser 155 | Ala | Asn | Leu | Gln | Glu 160 | Arg | Leu | Arg | Arg | Lys 165 | Glu | | | |

(2) INFORMATION FOR SEQ ID NO:8:

(i) SEQUENCE CHARACTERISTICS:
  (A) LENGTH: 189 amino acids
  (B) TYPE: amino acid
  (D) TOPOLOGY: unknown (ii) MOLECULE TYPE: protein (ix) FEATURE:
  (A) NAME/KEY: Protein
  (B) LOCATION: 24..189
  (D) OTHER INFORMATION: /note= "IFN-alpha-H1 (alpha-H2)"

(ix) FEATURE:
  (A) NAME/KEY: Modified-site
  (B) LOCATION: 123
  (D) OTHER INFORMATION: /note= "The identity of position 123 is inadvertently omitted in the sequence recited in Table 1 of the specification."

(xi) SEQUENCE DESCRIPTION: SEQ ID NO:8:

| | | | | | | | | | | | | | |
|---|---|---|---|---|---|---|---|---|---|---|---|---|---|
| Met | Ala | Leu | Pro -20 | Phe | Ser | Leu | Met | Met -15 | Ala | Leu | Val | Val | Leu -10 | Ser | Cys |
| Lys | Ser | Ser -5 | Cys | Ser | Leu | Gly | Cys 1 | Asn | Leu | Ser | Gln 5 | Thr | His | Ser | Leu |
| Asn 10 | Asn | Arg | Arg | Thr | Leu 15 | Met | Leu | Met | Ala | Gln 20 | Met | Arg | Arg | Ile | Ser 25 |
| Pro | Phe | Ser | Cys | Leu 30 | Lys | Xaa | Arg | His | Asp 35 | Phe | Glu | Phe | Pro | Gln 40 | Glu |
| Glu | Phe | Asp | Gly 45 | Asn | Gln | Phe | Gln | Lys 50 | Ala | Gln | Ala | Ile | Ser 55 | Val | Leu |
| His | Glu | Met 60 | Met | Gln | Gln | Thr | Phe 65 | Asn | Leu | Phe | Ser | Thr 70 | Lys | Asn | Ser |
| Ser | Ala 75 | Ala | Trp | Asp | Glu | Thr 80 | Leu | Leu | Glu | Lys | Phe 85 | Tyr | Ile | Glu | Leu |

```
         Phe  Gln  Met  Leu  Asn  Asp  Leu  Glu  Ala  Cys  Xaa  Xaa  Gln  Glu  Val  Gly
         90             95                      100                     105

Val  Glu  Glu  Thr  Pro  Leu  Met  Asn  Glu  Asp  Ser  Ile  Leu  Ala  Val  Lys
                            110                     115                     120

Lys  Tyr  Phe  Gln  Arg  Ile  Thr  Leu  Tyr  Met  Thr  Glu  Lys  Lys  Tyr  Ser
                            125                     130                     135

Pro  Cys  Ala  Trp  Glu  Val  Val  Arg  Ala  Glu  Ile  Met  Arg  Ser  Phe  Ser
                            140                     145                     150

Phe  Ser  Thr  Asn  Leu  Gln  Lys  Arg  Leu  Arg  Arg  Lys  Asp
                            155                     160                     165
```

( 2 ) INFORMATION FOR SEQ ID NO:9:

( i ) SEQUENCE CHARACTERISTICS:
        ( A ) LENGTH: 189 amino acids
        ( B ) TYPE: amino acid
        ( D ) TOPOLOGY: unknown ( i i ) MOLECULE TYPE: protein ( i x ) FEATURE:
        ( A ) NAME/KEY: Protein
        ( B ) LOCATION: 24..189
        ( D ) OTHER INFORMATION: /note= "IFN-alpha-B2 (alpha-8)"

( x i ) SEQUENCE DESCRIPTION: SEQ ID NO:9:

```
         Met  Ala  Leu  Thr  Phe  Tyr  Leu  Leu  Val  Ala  Leu  Val  Val  Leu  Ser  Tyr
                            -20                     -15                     -10

Lys  Ser  Phe  Ser  Ser  Leu  Gly  Cys  Asp  Leu  Pro  Gln  Thr  His  Ser  Leu
                            -5                      1                       5

Gly  Asn  Arg  Arg  Ala  Leu  Ile  Leu  Leu  Ala  Gln  Met  Arg  Arg  Ile  Ser
         10                       15                      20                      25

Pro  Phe  Ser  Cys  Leu  Lys  Xaa  Arg  His  Asp  Phe  Glu  Phe  Pro  Gln  Glu
                            30                      35                      40

Glu  Phe  Asp  Asp  Lys  Gln  Phe  Gln  Lys  Ala  Gln  Ala  Ile  Ser  Val  Leu
                            45                      50                      55

His  Glu  Met  Ile  Gln  Gln  Thr  Phe  Asn  Leu  Phe  Ser  Thr  Lys  Asp  Ser
                            60                      65                      70

Ser  Ala  Ala  Leu  Asp  Glu  Thr  Leu  Leu  Asp  Glu  Phe  Tyr  Ile  Glu  Leu
                  75                       80                      85

Asp  Gln  Gln  Leu  Asn  Asp  Leu  Glu  Ser  Cys  Val  Met  Gln  Glu  Val  Gly
         90                       95                      100                     105

Val  Ile  Glu  Ser  Pro  Leu  Met  Tyr  Glu  Asp  Ser  Ile  Leu  Ala  Val  Arg
                            110                     115                     120

Lys  Tyr  Phe  Gln  Arg  Ile  Thr  Leu  Tyr  Leu  Thr  Glu  Lys  Lys  Tyr  Ser
                            125                     130                     135

Ser  Cys  Ala  Trp  Glu  Val  Val  Arg  Ala  Glu  Ile  Met  Arg  Ser  Phe  Ser
                            140                     145                     150

Leu  Ser  Ile  Asn  Leu  Gln  Lys  Arg  Leu  Lys  Ser  Lys  Glu
                            155                     160                     165
```

( 2 ) INFORMATION FOR SEQ ID NO:10:

( i ) SEQUENCE CHARACTERISTICS:
        ( A ) LENGTH: 189 amino acids
        ( B ) TYPE: amino acid
        ( D ) TOPOLOGY: unknown ( i i ) MOLECULE TYPE: protein ( i x ) FEATURE:

( A ) NAME/KEY: Protein
( B ) LOCATION: 24..189
( D ) OTHER INFORMATION: /note= "IFN-alpha-B"

( x i ) SEQUENCE DESCRIPTION: SEQ ID NO:10:

```
Met Ala Leu Thr Phe Tyr Leu Met Val Ala Leu Val Val Leu Ser Tyr
            -20              -15                   -10
Lys Ser Phe Ser Ser Leu Gly Cys Asp Leu Pro Gln Thr His Ser Leu
         -5              1              5
Gly Asn Arg Arg Ala Leu Ile Leu Leu Ala Gln Met Arg Arg Ile Ser
 10               15                   20                    25
Pro Phe Ser Cys Leu Lys Xaa Arg His Asp Phe Glu Phe Pro Gln Glu
             30              35                  40
Glu Phe Asp Asp Lys Gln Phe Gln Lys Ala Gln Ala Ile Ser Val Leu
             45              50                  55
His Glu Met Ile Gln Gln Thr Phe Asn Leu Phe Ser Thr Lys Asp Ser
         60              65              70
Ser Ala Ala Leu Asp Glu Thr Leu Leu Asp Glu Phe Tyr Ile Glu Leu
     75              80              85
Asp Gln Gln Leu Asn Asp Leu Glu Val Leu Cys Asp Gln Glu Val Gly
 90               95              100                       105
Val Ile Glu Ser Pro Leu Met Tyr Glu Asp Ser Ile Leu Ala Val Arg
             110             115                         120
Lys Tyr Phe Gln Arg Ile Thr Leu Tyr Leu Thr Glu Lys Lys Tyr Ser
             125             130                 135
Ser Cys Ala Trp Glu Val Val Arg Ala Glu Ile Met Arg Ser Phe Ser
             140             145                 150
Leu Ser Ile Asn Leu Gln Lys Arg Leu Lys Ser Lys Glu
             155             160                 165
```

( 2 ) INFORMATION FOR SEQ ID NO:11:

( i ) SEQUENCE CHARACTERISTICS:
( A ) LENGTH: 189 amino acids
( B ) TYPE: amino acid
( D ) TOPOLOGY: unknown ( i i ) MOLECULE TYPE: protein ( i x ) FEATURE:
( A ) NAME/KEY: Protein
( B ) LOCATION: 24..189
( D ) OTHER INFORMATION: /note= "IFN-alpha-4b"

( x i ) SEQUENCE DESCRIPTION: SEQ ID NO:11:

```
Met Ala Leu Ser Phe Ser Leu Leu Met Ala Val Leu Val Leu Ser Tyr
            -20              -15                   -10
Lys Ser Ile Cys Ser Leu Gly Cys Asp Leu Pro Gln Thr His Ser Leu
         -5              1              5
Gly Asn Arg Arg Ala Leu Ile Leu Leu Ala Gln Met Gly Arg Ile Ser
 10               15                   20                    25
His Phe Ser Cys Leu Lys Xaa Arg His Asp Phe Gly Phe Pro Glu Glu
             30              35                  40
Glu Phe Asp Gly His Gln Phe Gln Lys Thr Gln Ala Ile Ser Val Leu
             45              50                  55
His Glu Met Ile Gln Gln Thr Phe Asn Leu Phe Ser Thr Glu Asp Ser
         60              65              70
Ser Ala Ala Trp Glu Gln Ser Leu Leu Glu Lys Phe Ser Thr Glu Leu
     75              80              85
```

```
Tyr Gln Gln Leu Asn Asp Leu Glu Ala Cys Val Xaa Gln Glu Val Gly
 90              95                 100                    105

Val Glu Glu Thr Pro Leu Met Asn Val Asp Ser Ile Leu Ala Val Arg
                110             115                     120

Lys Tyr Phe Gln Arg Ile Thr Leu Tyr Leu Thr Glu Lys Lys Tyr Ser
            125                 130             135

Pro Cys Ala Trp Glu Val Val Arg Ala Glu Ile Met Arg Ser Leu Ser
        140             145                 150

Phe Ser Thr Asn Leu Gln Lys Arg Leu Arg Arg Lys Asp
    155             160                 165
```

( 2 ) INFORMATION FOR SEQ ID NO:12:

( i ) SEQUENCE CHARACTERISTICS:
        ( A ) LENGTH: 189 amino acids
        ( B ) TYPE: amino acid
        ( D ) TOPOLOGY: unknown ( i i ) MOLECULE TYPE: protein ( i x ) FEATURE:
        ( A ) NAME/KEY: Protein
        ( B ) LOCATION: 24..189
        ( D ) OTHER INFORMATION: /note= "IFN-alpha-C"

( x i ) SEQUENCE DESCRIPTION: SEQ ID NO:12:

```
Met Ala Leu Ser Phe Ser Leu Leu Met Ala Val Leu Val Leu Ser Tyr
        -20                 -15                 -10

Lys Ser Ile Cys Ser Leu Gly Cys Asp Leu Pro Gln Thr His Ser Leu
         -5              1              5

Gly Asn Arg Arg Ala Leu Ile Leu Leu Gly Gln Met Gly Arg Ile Ser
 10              15              20                      25

Pro Phe Ser Cys Leu Lys Xaa Arg His Asp Phe Arg Ile Pro Gln Glu
            30                  35                      40

Glu Phe Asp Gly Asn Gln Phe Gln Lys Ala Gln Ala Ile Ser Val Leu
            45              50                      55

His Glu Met Ile Gln Gln Thr Phe Asn Leu Phe Ser Thr Glu Asp Ser
        60              65                  70

Ser Ala Ala Trp Glu Gln Ser Leu Leu Glu Lys Phe Ser Thr Glu Leu
 75              80                  85

Tyr Gln Gln Leu Asn Asp Leu Glu Ala Cys Val Xaa Gln Glu Val Gly
 90              95                 100                    105

Val Glu Glu Thr Pro Leu Met Asn Glu Asp Ser Ile Leu Ala Val Arg
                110             115                     120

Lys Tyr Phe Gln Arg Ile Thr Leu Tyr Leu Ile Glu Arg Lys Tyr Ser
            125                 130             135

Pro Cys Ala Trp Glu Val Val Arg Ala Glu Ile Met Arg Ser Leu Ser
        140             145                 150

Phe Ser Thr Asn Leu Gln Lys Arg Leu Arg Arg Lys Asp
    155             160                 165
```

( 2 ) INFORMATION FOR SEQ ID NO:13:

( i ) SEQUENCE CHARACTERISTICS:
        ( A ) LENGTH: 189 amino acids
        ( B ) TYPE: amino acid
        ( D ) TOPOLOGY: unknown ( i i ) MOLECULE TYPE: protein ( i x ) FEATURE:
        ( A ) NAME/KEY: Protein (B) LOCATION: 24..189
(D) OTHER INFORMATION: /note= "IFN-alpha-L (beta-alpha-10)"

(xi) SEQUENCE DESCRIPTION: SEQ ID NO:13:

| | | | | | | | | | | | | | | |
|---|---|---|---|---|---|---|---|---|---|---|---|---|---|---|
| Met | Ala | Leu | Ser -20 | Phe | Ser | Leu | Leu | Met -15 | Ala | Val | Leu | Val | Leu -10 | Ser | Tyr |
| Lys | Ser | Ile -5 | Cys | Ser | Leu | Gly | Cys 1 | Asp | Leu | Pro | Gln 5 | Thr | His | Thr | Leu |
| Arg 10 | Asn | Arg | Arg | Ala | Leu 15 | Ile | Leu | Leu | Gly | Gln 20 | Met | Gly | Arg | Ile | Ser 25 |
| Pro | Phe | Ser | Cys | Leu 30 | Lys | Xaa | Arg | His | Asp 35 | Phe | Arg | Ile | Pro | Gln 40 | Glu |
| Glu | Phe | Asp | Gly 45 | Asn | Gln | Phe | Gln | Lys 50 | Ala | Gln | Ala | Ile | Ser 55 | Val | Leu |
| His | Glu | Met 60 | Ile | Gln | Gln | Thr | Phe 65 | Asn | Leu | Phe | Ser | Thr 70 | Glu | Asp | Ser |
| Ser | Ala 75 | Ala | Trp | Glu | Gln | Ser 80 | Leu | Leu | Glu | Lys | Phe 85 | Ser | Thr | Glu | Ile |
| Tyr 90 | Gln | Gln | Leu | Asn | Asp 95 | Leu | Glu | Ala | Cys | Val 100 | Xaa | Gln | Glu | Val | Gly 105 |
| Val | Glu | Glu | Thr | Pro 110 | Leu | Met | Asn | Glu | Asp 115 | Ser | Ile | Leu | Ala | Val 120 | Arg |
| Lys | Tyr | Phe | Gln 125 | Arg | Ile | Thr | Leu | Tyr 130 | Leu | Ile | Glu | Arg | Lys 135 | Tyr | Ser |
| Pro | Cys | Ala 140 | Trp | Glu | Val | Val | Arg 145 | Ala | Glu | Ile | Met | Arg 150 | Ser | Leu | Ser |
| Phe | Ser 155 | Thr | Asn | Leu | Gln | Lys 160 | Arg | Leu | Arg | Arg | Lys 165 | Asp | | | |

(2) INFORMATION FOR SEQ ID NO:14:

(i) SEQUENCE CHARACTERISTICS:
(A) LENGTH: 189 amino acids
(B) TYPE: amino acid
(D) TOPOLOGY: unknown (ii) MOLECULE TYPE: protein (ix) FEATURE:
(A) NAME/KEY: Protein
(B) LOCATION: 24..189
(D) OTHER INFORMATION: /note= "IFN-alpha-J1 (alpha-7)"

(xi) SEQUENCE DESCRIPTION: SEQ ID NO:14:

| | | | | | | | | | | | | | | |
|---|---|---|---|---|---|---|---|---|---|---|---|---|---|---|
| Met | Ala | Arg | Ser -20 | Phe | Ser | Leu | Leu | Met -15 | Val | Val | Leu | Val | Leu -10 | Ser | Tyr |
| Lys | Ser | Ile -5 | Cys | Ser | Leu | Gly | Cys 1 | Asp | Leu | Pro | Gln 5 | Thr | His | Ser | Leu |
| Arg 10 | Asn | Arg | Arg | Ala | Leu 15 | Ile | Leu | Leu | Ala | Gln 20 | Met | Gly | Arg | Ile | Ser 25 |
| Pro | Phe | Ser | Cys | Leu 30 | Lys | Xaa | Arg | His | Glu 35 | Phe | Arg | Phe | Pro | Glu 40 | Glu |
| Glu | Phe | Asp | Gly 45 | His | Gln | Phe | Gln | Lys 50 | Thr | Gln | Ala | Ile | Ser 55 | Val | Leu |
| His | Glu | Met 60 | Ile | Gln | Gln | Thr | Phe 65 | Asn | Leu | Phe | Ser | Thr 70 | Glu | Asp | Ser |
| Ser | Ala 75 | Ala | Trp | Glu | Gln | Ser 80 | Leu | Leu | Glu | Lys | Phe 85 | Ser | Thr | Glu | Leu |
| Tyr | Gln | Gln | Leu | Asn | Asp | Leu | Glu | Ala | Cys | Val | Xaa | Gln | Glu | Val | Gly |

|     |     |     |     |     | 90  |     |     |     |     | 95  |     |     |     |     | 100 |     |     |     |     | 105 |
|-----|-----|-----|-----|-----|-----|-----|-----|-----|-----|-----|-----|-----|-----|-----|-----|-----|-----|-----|-----|-----|

Val Glu Glu Thr Pro Leu Met Asn Glu Asp Phe Ile Leu Ala Val Arg
                    110             115                 120

Lys Tyr Phe Gln Arg Ile Thr Leu Tyr Leu Met Glu Lys Lys Tyr Ser
            125             130             135

Pro Cys Ala Trp Glu Val Val Arg Ala Glu Ile Met Arg Ser Phe Ser
        140             145             150

Phe Ser Thr Asn Leu Lys Lys Gly Leu Arg Arg Lys Asp
    155             160             165

(2) INFORMATION FOR SEQ ID NO:15:

(i) SEQUENCE CHARACTERISTICS:
      (A) LENGTH: 189 amino acids
      (B) TYPE: amino acid
      (D) TOPOLOGY: unknown (ii) MOLECULE TYPE: protein (ix) FEATURE:
      (A) NAME/KEY: Protein
      (B) LOCATION: 24..189
      (D) OTHER INFORMATION: /note= "IFN-alpha-J2"

(xi) SEQUENCE DESCRIPTION: SEQ ID NO:15:

Met Ala Arg Ser Phe Ser Leu Leu Met Val Val Leu Val Leu Ser Tyr
            -20             -15             -10

Lys Ser Ile Cys Ser Leu Gly Cys Asp Leu Pro Gln Thr His Ser Leu
        -5               1               5

Arg Asn Arg Arg Ala Leu Ile Leu Leu Ala Gln Met Gly Arg Ile Ser
10              15              20                              25

Pro Phe Ser Cys Leu Lys Xaa Arg His Glu Phe Arg Phe Pro Glu Glu
            30              35                              40

Glu Phe Asp Gly His Gln Phe Gln Lys Thr Gln Ala Ile Ser Val Leu
            45              50                      55

His Glu Met Ile Gln Gln Thr Phe Asn Leu Phe Ser Thr Glu Asp Ser
        60              65                      70

Ser Ala Ala Trp Glu Gln Ser Leu Leu Glu Lys Phe Ser Thr Glu Leu
    75              80                      85

Tyr Gln Gln Leu Asn Asp Leu Glu Ala Cys Val Xaa Gln Glu Val Gly
90              95                      100                     105

Val Glu Glu Thr Pro Leu Met Asn Glu Asp Phe Ile Leu Ala Val Arg
                    110             115                 120

Lys Tyr Phe Gln Arg Ile Thr Leu Tyr Leu Met Glu Lys Lys Tyr Ser
            125             130             135

Pro Cys Ala Trp Glu Val Val Arg Ala Glu Ile Met Arg Ser Phe Ser
        140             145             150

Phe Ser Thr Asn Leu Gln Lys Arg Leu Arg Arg Lys Asp
    155             160             165

(2) INFORMATION FOR SEQ ID NO:16:

(i) SEQUENCE CHARACTERISTICS:
      (A) LENGTH: 189 amino acids
      (B) TYPE: amino acid
      (D) TOPOLOGY: unknown (ii) MOLECULE TYPE: protein (ix) FEATURE:
      (A) NAME/KEY: Protein
      (B) LOCATION: 24..189

( D ) OTHER INFORMATION: /note= "IFN-alpha-F"

( x i ) SEQUENCE DESCRIPTION: SEQ ID NO:16:

| Met | Ala | Leu | Ser -20 | Phe | Ser | Leu | Leu | Met -15 | Ala | Val | Leu | Val | Leu -10 | Ser | Tyr |
|---|---|---|---|---|---|---|---|---|---|---|---|---|---|---|---|
| Lys | Ser | Ile | Cys -5 | Ser | Leu | Gly | Cys | Asp 1 | Leu | Pro | Gln | Thr 5 | His | Ser | Leu |
| Gly 10 | Asn | Arg | Arg | Ala | Leu 15 | Ile | Leu | Leu | Ala | Gln 20 | Met | Gly | Arg | Ile | Ser 25 |
| Pro | Phe | Ser | Cys | Leu 30 | Lys | Xaa | Arg | Pro | Asp 35 | Phe | Leu | Phe | Pro | Gln 40 | Glu |
| Glu | Phe | Asp | Gly 45 | Asn | Gln | Phe | Gln | Lys 50 | Thr | Gln | Ala | Ile | Ser 55 | Val | Leu |
| His | Glu | Met 60 | Ile | Gln | Gln | Thr | Phe 65 | Asn | Leu | Phe | Ser | Thr 70 | Glu | Asp | Ser |
| Ser | Ala 75 | Ala | Trp | Glu | Gln | Ser 80 | Leu | Leu | Glu | Lys | Phe 85 | Ser | Thr | Glu | Leu |
| Tyr 90 | Gln | Gln | Leu | Asn | Asn 95 | Leu | Glu | Ala | Cys | Val 100 | Xaa | Gln | Glu | Val | Gly 105 |
| Met | Glu | Glu | Thr | Pro 110 | Leu | Met | Asn | Glu | Asp 115 | Ser | Ile | Leu | Ala | Val 120 | Arg |
| Lys | Tyr | Phe | Gln 125 | Arg | Ile | Thr | Leu | Tyr 130 | Leu | Thr | Glu | Lys | Lys 135 | Tyr | Ser |
| Pro | Cys | Ala 140 | Trp | Glu | Val | Val | Arg 145 | Ala | Glu | Ile | Met | Arg 150 | Ser | Leu | Ser |
| Phe | Ser 155 | Thr | Asn | Leu | Gln | Lys 160 | Ile | Leu | Arg | Arg | Lys 165 | Asp | | | |

( 2 ) INFORMATION FOR SEQ ID NO:17:

( i ) SEQUENCE CHARACTERISTICS:
        ( A ) LENGTH: 189 amino acids
        ( B ) TYPE: amino acid
        ( D ) TOPOLOGY: unknown ( i i ) MOLECULE TYPE: protein ( i x ) FEATURE:
        ( A ) NAME/KEY: Protein
        ( B ) LOCATION: 24..189
        ( D ) OTHER INFORMATION: /note= "IFN-alpha-F"

( x i ) SEQUENCE DESCRIPTION: SEQ ID NO:17:

| Met | Ala | Leu | Ser -20 | Phe | Ser | Leu | Leu | Met -15 | Ala | Val | Leu | Val | Leu -10 | Ser | Tyr |
|---|---|---|---|---|---|---|---|---|---|---|---|---|---|---|---|
| Lys | Ser | Ile | Cys -5 | Ser | Leu | Gly | Cys | Asp 1 | Leu | Pro | Gln | Thr 5 | His | Ser | Leu |
| Gly 10 | Asn | Arg | Arg | Ala | Leu 15 | Ile | Leu | Leu | Ala | Gln 20 | Met | Gly | Arg | Ile | Ser 25 |
| Pro | Phe | Ser | Cys | Leu 30 | Lys | Xaa | Arg | His | Asp 35 | Phe | Gly | Phe | Pro | Gln 40 | Glu |
| Glu | Phe | Asp | Gly 45 | Asn | Gln | Phe | Gln | Lys 50 | Ala | Gln | Ala | Ile | Ser 55 | Val | Leu |
| His | Glu | Met 60 | Ile | Gln | Gln | Thr | Phe 65 | Asn | Leu | Phe | Ser | Thr 70 | Lys | Asp | Ser |
| Ser | Ala 75 | Thr | Trp | Glu | Gln | Ser 80 | Leu | Leu | Glu | Lys | Phe 85 | Ser | Thr | Glu | Leu |
| Asn 90 | Gln | Gln | Leu | Asn | Asp 95 | Met | Glu | Ala | Cys | Val 100 | Xaa | Gln | Glu | Val | Gly 105 |

-continued

```
Val Glu Glu Thr Pro Leu Met Asn Val Asp Ser Ile Leu Ala Val Lys
                110                 115                 120

Lys Tyr Phe Gln Arg Ile Thr Leu Tyr Leu Thr Glu Lys Lys Tyr Ser
                125                 130                 135

Pro Cys Ala Trp Glu Val Val Arg Ala Glu Ile Met Arg Ser Phe Ser
                140                 145                 150

Leu Ser Lys Ile Phe Gln Glu Arg Leu Arg Arg Lys Glu
                155                 160                 165
```

(2) INFORMATION FOR SEQ ID NO:18:

(i) SEQUENCE CHARACTERISTICS:
    (A) LENGTH: 189 amino acids
    (B) TYPE: amino acid
    (D) TOPOLOGY: unknown (ii) MOLECULE TYPE: protein (ix) FEATURE:
    (A) NAME/KEY: Protein
    (B) LOCATION: 24..189
    (D) OTHER INFORMATION: /note= "IFN-alpha-WA"

(xi) SEQUENCE DESCRIPTION: SEQ ID NO:18:

```
Met Ala Leu Ser Phe Ser Leu Leu Met Ala Val Leu Val Leu Ser Tyr
            -20                 -15                 -10

Lys Ser Ile Cys Ser Leu Gly Cys Asp Leu Pro Gln Thr His Ser Leu
             -5                   1                   5

Gly Asn Arg Arg Ala Leu Ile Leu Leu Ala Gln Met Gly Arg Ile Ser
 10                  15                  20                  25

His Phe Ser Cys Leu Lys Xaa Arg Tyr Asp Phe Gly Phe Pro Gln Glu
                 30                  35                  40

Val Phe Asp Gly Asn Gln Phe Gln Lys Ala Gln Ala Ile Ser Ala Phe
                 45                  50                  55

His Glu Met Ile Gln Gln Thr Phe Asn Leu Phe Ser Thr Lys Asp Ser
             60                  65                  70

Ser Ala Ala Trp Asp Glu Thr Leu Leu Asp Lys Phe Tyr Ile Glu Leu
 75                  80                  85

Phe Gln Gln Leu Asn Asp Leu Glu Ala Cys Val Thr Gln Glu Val Gly
 90                  95                 100                 105

Val Glu Glu Ile Ala Leu Met Asn Glu Asp Ser Ile Leu Ala Val Arg
                110                 115                 120

Lys Tyr Phe Gln Arg Ile Thr Leu Tyr Leu Met Gly Lys Lys Tyr Ser
                125                 130                 135

Pro Cys Ala Trp Glu Val Val Arg Ala Glu Ile Met Arg Ser Phe Ser
                140                 145                 150

Phe Ser Thr Asn Leu Gln Lys Gly Leu Arg Arg Lys Asp
                155                 160                 165
```

(2) INFORMATION FOR SEQ ID NO:19:

(i) SEQUENCE CHARACTERISTICS:
    (A) LENGTH: 189 amino acids
    (B) TYPE: amino acid
    (D) TOPOLOGY: unknown (ii) MOLECULE TYPE: protein (ix) FEATURE:
    (A) NAME/KEY: Protein
    (B) LOCATION: 24..189
    (D) OTHER INFORMATION: /note= "IFN-alpha-Gk-1"

( x i ) SEQUENCE DESCRIPTION: SEQ ID NO:19:

| Met | Ala | Leu | Pro | Phe | Ser | Leu | Met | Met | Ala | Leu | Val | Val | Leu | Ser | Cys |
| --- | --- | --- | --- | --- | --- | --- | --- | --- | --- | --- | --- | --- | --- | --- | --- |
|  |  |  | -20 |  |  |  |  | -15 |  |  |  |  | -10 |  |  |
| Lys | Ser | Ser | Cys | Ser | Leu | Gly | Cys | Asn | Leu | Ser | Gln | Thr | His | Ser | Leu |
|  |  | -5 |  |  |  |  | 1 |  |  |  | 5 |  |  |  |  |
| Asn | Asn | Arg | Arg | Thr | Leu | Met | Ile | Leu | Ala | Gln | Met | Gly | Arg | Ile | Ser |
| 10 |  |  |  |  | 15 |  |  |  |  | 20 |  |  |  |  | 25 |
| Pro | Phe | Ser | Cys | Leu | Lys | Xaa | Arg | His | Asp | Phe | Gly | Phe | Pro | Gln | Glu |
|  |  |  |  | 30 |  |  |  |  | 35 |  |  |  |  | 40 |  |
| Glu | Phe | Asp | Gly | Asn | Gln | Phe | Gln | Lys | Ala | Gln | Ala | Ile | Ser | Val | Leu |
|  |  |  | 45 |  |  |  |  | 50 |  |  |  |  | 55 |  |  |
| His | Glu | Met | Ile | Gln | Gln | Thr | Phe | Asn | Leu | Phe | Ser | Thr | Lys | Asp | Ser |
|  |  | 60 |  |  |  |  | 65 |  |  |  |  | 70 |  |  |  |
| Ser | Ala | Thr | Trp | Asp | Glu | Thr | Leu | Leu | Asp | Lys | Phe | Tyr | Thr | Glu | Leu |
|  | 75 |  |  |  |  | 80 |  |  |  |  | 85 |  |  |  |  |
| Tyr | Gln | Gln | Leu | Asn | Asp | Leu | Glu | Ala | Cys | Met | Met | Gln | Glu | Val | Gly |
| 90 |  |  |  |  | 95 |  |  |  |  | 100 |  |  |  |  | 105 |
| Val | Glu | Asp | Thr | Pro | Leu | Met | Asn | Val | Asp | Ser | Ile | Leu | Thr | Val | Arg |
|  |  |  |  | 110 |  |  |  |  | 115 |  |  |  |  | 120 |  |
| Lys | Tyr | Phe | Gln | Arg | Ile | Thr | Leu | Tyr | Leu | Thr | Glu | Lys | Lys | Tyr | Ser |
|  |  |  | 125 |  |  |  |  | 130 |  |  |  |  | 135 |  |  |
| Pro | Cys | Ala | Trp | Glu | Val | Val | Arg | Ala | Glu | Ile | Met | Arg | Ser | Phe | Ser |
|  |  | 140 |  |  |  |  | 145 |  |  |  |  | 150 |  |  |  |
| Leu | Ser | Ala | Asn | Leu | Gln | Glu | Arg | Leu | Arg | Arg | Lys | Glu |  |  |  |
|  | 155 |  |  |  |  | 160 |  |  |  |  | 165 |  |  |  |  |

( 2 ) INFORMATION FOR SEQ ID NO:20:

( i ) SEQUENCE CHARACTERISTICS:
( A ) LENGTH: 189 amino acids
( B ) TYPE: amino acid
( D ) TOPOLOGY: unknown ( i i ) MOLECULE TYPE: protein ( i x ) FEATURE:
( A ) NAME/KEY: Protein
( B ) LOCATION: 24..189
( D ) OTHER INFORMATION: /note= "IFN-alpha-76"

( x i ) SEQUENCE DESCRIPTION: SEQ ID NO:20:

| Met | Ala | Leu | Ser | Phe | Ser | Leu | Leu | Met | Ala | Val | Leu | Val | Leu | Ser | Tyr |
| --- | --- | --- | --- | --- | --- | --- | --- | --- | --- | --- | --- | --- | --- | --- | --- |
|  |  |  | -20 |  |  |  |  | -15 |  |  |  |  | -10 |  |  |
| Lys | Ser | Ile | Cys | Ser | Leu | Gly | Cys | Asp | Leu | Pro | Gln | Thr | His | Ser | Leu |
|  |  | -5 |  |  |  |  | 1 |  |  |  | 5 |  |  |  |  |
| Gly | Asn | Arg | Arg | Ala | Leu | Ile | Leu | Leu | Ala | Gln | Met | Gly | Arg | Ile | Ser |
| 10 |  |  |  |  | 15 |  |  |  |  | 20 |  |  |  |  | 25 |
| His | Phe | Ser | Cys | Leu | Lys | Xaa | Arg | His | Asp | Phe | Gly | Phe | Pro | Glu | Glu |
|  |  |  |  | 30 |  |  |  |  | 35 |  |  |  |  | 40 |  |
| Glu | Phe | Asp | Gly | His | Gln | Phe | Gln | Lys | Ala | Gln | Ala | Ile | Ser | Val | Leu |
|  |  |  | 45 |  |  |  |  | 50 |  |  |  |  | 55 |  |  |
| His | Glu | Met | Ile | Gln | Gln | Thr | Phe | Asn | Leu | Phe | Ser | Thr | Glu | Asp | Ser |
|  |  | 60 |  |  |  |  | 65 |  |  |  |  | 70 |  |  |  |
| Ser | Ala | Ala | Trp | Glu | Gln | Ser | Leu | Leu | Glu | Lys | Phe | Ser | Thr | Glu | Leu |
|  | 75 |  |  |  |  | 80 |  |  |  |  | 85 |  |  |  |  |
| Tyr | Gln | Gln | Leu | Asn | Asp | Leu | Glu | Ala | Cys | Val | Xaa | Gln | Glu | Val | Gly |
| 90 |  |  |  |  | 95 |  |  |  |  | 100 |  |  |  |  | 105 |

```
Val  Glu  Glu  Thr  Pro  Leu  Met  Asn  Glu  Asp  Ser  Ile  Leu  Ala  Val  Arg
                    110                 115                      120

Lys  Tyr  Phe  Gln  Arg  Ile  Thr  Leu  Tyr  Leu  Thr  Glu  Lys  Lys  Tyr  Ser
               125                      130                      135

Pro  Cys  Ala  Trp  Glu  Val  Val  Arg  Ala  Glu  Ile  Met  Arg  Ser  Leu  Ser
          140                      145                      150

Phe  Ser  Thr  Asn  Leu  Gln  Lys  Arg  Leu  Arg  Arg  Lys  Asp
     155                 160                      165
```

( 2 ) INFORMATION FOR SEQ ID NO:21:

( i ) SEQUENCE CHARACTERISTICS:
        ( A ) LENGTH: 187 amino acids
        ( B ) TYPE: amino acid
        ( D ) TOPOLOGY: unknown ( i i ) MOLECULE TYPE: protein ( i x ) FEATURE:
        ( A ) NAME/KEY: Protein
        ( B ) LOCATION: 22..187
        ( D ) OTHER INFORMATION: /note= "IFN-beta consensus"

( x i ) SEQUENCE DESCRIPTION: SEQ ID NO:21:

```
Met  Thr  Xaa  Arg  Cys  Leu  Leu  Gln  Xaa  Ala  Leu  Leu  Leu  Cys  Phe  Ser
     -20                      -15                      -10

Thr  Thr  Ala  Leu  Ser  Xaa  Ser  Tyr  Xaa  Leu  Leu  Xaa  Phe  Gln  Gln  Arg
-5                        1               5                           10

Xaa  Ser  Xaa  Xaa  Xaa  Cys  Gln  Lys  Leu  Leu  Xaa  Gln  Leu  Xaa  Xaa  Xaa
               15                      20                      25

Xaa  Xaa  Xaa  Cys  Leu  Xaa  Xaa  Arg  Met  Asp  Phe  Xaa  Xaa  Pro  Glu  Glu
          30                      35                      40

Met  Lys  Gln  Xaa  Gln  Gln  Phe  Gln  Lys  Glu  Asp  Ala  Ala  Leu  Xaa  Ile
     45                      50                      55

Tyr  Glu  Met  Leu  Gln  Asn  Ile  Phe  Xaa  Ile  Phe  Arg  Xaa  Asp  Phe  Ser
60                        65                 70                           75

Ser  Thr  Gly  Trp  Asn  Glu  Thr  Ile  Val  Glu  Xaa  Leu  Leu  Xaa  Glu  Leu
               80                      85                      90

Tyr  Xaa  Gln  Xaa  Asn  Xaa  Leu  Lys  Thr  Val  Leu  Glu  Glu  Lys  Xaa  Glu
          95                      100                     105

Lys  Glu  Asn  Xaa  Thr  Xaa  Gly  Xaa  Xaa  Met  Ser  Ser  Leu  His  Leu  Lys
               110                     115                     120

Xaa  Tyr  Tyr  Xaa  Arg  Xaa  Xaa  Xaa  Tyr  Leu  Lys  Xaa  Lys  Glu  Tyr  Xaa
     125                     130                     135

Xaa  Cys  Ala  Trp  Thr  Val  Val  Arg  Val  Glu  Ile  Leu  Arg  Asn  Phe  Xaa
140                      145                     150                     155

Phe  Ile  Xaa  Arg  Leu  Thr  Gly  Tyr  Leu  Arg  Asn
               160                     165
```

( 2 ) INFORMATION FOR SEQ ID NO:22:

( i ) SEQUENCE CHARACTERISTICS:
        ( A ) LENGTH: 187 amino acids
        ( B ) TYPE: amino acid
        ( D ) TOPOLOGY: unknown ( i i ) MOLECULE TYPE: protein ( i x ) FEATURE:
        ( A ) NAME/KEY: Protein
        ( B ) LOCATION: 22..187
        ( D ) OTHER INFORMATION: /note= "Hu-IFN-beta"

( x i ) SEQUENCE DESCRIPTION: SEQ ID NO:22:

| Met | Thr | Asn | Lys | Cys | Leu | Leu | Gln | Ile | Ala | Leu | Leu | Leu | Cys | Phe | Ser |
|---|---|---|---|---|---|---|---|---|---|---|---|---|---|---|---|
| | -20 | | | | | -15 | | | | | -10 | | | | |
| Thr | Thr | Ala | Leu | Ser | Met | Ser | Tyr | Asn | Leu | Leu | Gly | Phe | Leu | Gln | Arg |
| -5 | | | | | 1 | | | 5 | | | | | | 10 | |
| Ser | Ser | Asn | Phe | Gln | Cys | Gln | Lys | Leu | Leu | Trp | Gln | Leu | Asn | Gly | Arg |
| | | | 15 | | | | 20 | | | | | 25 | | | |
| Leu | Glu | Tyr | Cys | Leu | Lys | Asp | Arg | Met | Asn | Phe | Asp | Ile | Pro | Glu | Glu |
| | | 30 | | | | | 35 | | | | | 40 | | | |
| Ile | Lys | Gln | Leu | Gln | Gln | Phe | Gln | Lys | Glu | Asp | Ala | Ala | Leu | Thr | Ile |
| | 45 | | | | 50 | | | | | | 55 | | | | |
| Tyr | Glu | Met | Leu | Gln | Asn | Ile | Phe | Ala | Ile | Phe | Arg | Gln | Asp | Ser | Ser |
| 60 | | | | | 65 | | | | | 70 | | | | | 75 |
| Ser | Thr | Gly | Trp | Asn | Glu | Thr | Ile | Val | Glu | Asn | Leu | Leu | Ala | Asn | Val |
| | | | | 80 | | | | | 85 | | | | | 90 | |
| Tyr | Asx | Gln | Ile | Asn | His | Leu | Lys | Thr | Val | Leu | Glu | Glu | Lys | Leu | Glu |
| | | | 95 | | | | | | 100 | | | | 105 | | |
| Lys | Glu | Asp | Phe | Thr | Arg | Gly | Lys | Leu | Met | Ser | Ser | Leu | His | Leu | Lys |
| | | 110 | | | | | 115 | | | | | 120 | | | |
| Arg | Tyr | Tyr | Gly | Arg | Ile | Leu | His | Tyr | Leu | Lys | Ala | Lys | Glu | Tyr | Ser |
| | 125 | | | | | 130 | | | | | 135 | | | | |
| His | Cys | Ala | Trp | Thr | Ile | Val | Arg | Val | Glu | Ile | Leu | Arg | Asn | Phe | Tyr |
| 140 | | | | | 145 | | | | | 150 | | | | | 155 |
| Phe | Ile | Asn | Arg | Leu | Thr | Gly | Tyr | Leu | Arg | Asn | | | | | |
| | | | | 160 | | | | | 165 | | | | | | |

( 2 ) INFORMATION FOR SEQ ID NO:23:

( i ) SEQUENCE CHARACTERISTICS:
 ( A ) LENGTH: 186 amino acids
 ( B ) TYPE: amino acid
 ( D ) TOPOLOGY: unknown ( i i ) MOLECULE TYPE: protein ( i x ) FEATURE:
 ( A ) NAME/KEY: Protein
 ( B ) LOCATION: 22..186
 ( D ) OTHER INFORMATION: /note= "Mu-IFN-beta"

( x i ) SEQUENCE DESCRIPTION: SEQ ID NO:23:

| Met | Asn | Asn | Arg | Trp | Ile | Leu | His | Ala | Ala | Phe | Leu | Leu | Cys | Phe | Ser |
|---|---|---|---|---|---|---|---|---|---|---|---|---|---|---|---|
| | -20 | | | | | -15 | | | | | -10 | | | | |
| Thr | Thr | Ala | Leu | Ser | Ile | Asn | Tyr | Lys | Gln | Leu | Gln | Leu | Gln | Glu | Arg |
| -5 | | | | | 1 | | | 5 | | | | | | 10 | |
| Thr | Asn | Ile | Arg | Lys | Cys | Gln | Glu | Leu | Leu | Glu | Gln | Leu | Asn | Gly | Lys |
| | | | 15 | | | | 20 | | | | | 25 | | | |
| Ile | Xaa | Xaa | Asn | Leu | Thr | Tyr | Arg | Ala | Asp | Phe | Lys | Ile | Pro | Glu | Glu |
| | | 30 | | | | | 35 | | | | | 40 | | | |
| Met | Thr | Glu | Xaa | Lys | Met | Phe | Gln | Lys | Ser | Tyr | Thr | Ala | Phe | Ala | Ile |
| | 45 | | | | 50 | | | | | | 55 | | | | |
| Gln | Glu | Met | Leu | Gln | Asn | Val | Phe | Leu | Val | Phe | Arg | Asn | Asn | Phe | Ser |
| 60 | | | | | 65 | | | | | 70 | | | | | 75 |
| Ser | Thr | Gly | Trp | Asn | Glu | Thr | Ile | Val | Val | Arg | Leu | Leu | Asp | Glu | Leu |
| | | | | 80 | | | | | 85 | | | | | 90 | |
| His | Gln | Gln | Thr | Val | Phe | Leu | Lys | Thr | Val | Leu | Glu | Glu | Lys | Gln | Glu |
| | | | 95 | | | | | | 100 | | | | 105 | | |
| Glu | Arg | Leu | Thr | Trp | Glu | Met | Ser | Ser | Thr | Ala | Leu | His | Leu | Lys | Ser |

```
                    110                       115                           120
    Tyr   Tyr   Trp   Arg   Val   Gln   Arg   Tyr   Leu   Lys   Leu   Met   Lys   Tyr   Asn   Ser
          125                           130                     135

Tyr   Ala   Trp   Met   Val   Val   Arg   Ala   Glu   Ile   Phe   Arg   Asn   Phe   Leu   Ile
    140                     145                           150                                 155

Ile   Arg   Arg   Leu   Thr   Arg   Asn   Phe   Gln   Asn
                            160                     165
```

( 2 ) INFORMATION FOR SEQ ID NO:24:

( i ) SEQUENCE CHARACTERISTICS:
        ( A ) LENGTH: 186 amino acids
        ( B ) TYPE: amino acid
        ( D ) TOPOLOGY: unknown ( i i ) MOLECULE TYPE: protein ( i x ) FEATURE:
        ( A ) NAME/KEY: Protein
        ( B ) LOCATION: 22..186
        ( D ) OTHER INFORMATION: /note= "Bo-IFN-beta-1"

( x i ) SEQUENCE DESCRIPTION: SEQ ID NO:24:

```
    Met   Thr   Tyr   Arg   Cys   Leu   Leu   Gln   Met   Val   Leu   Leu   Leu   Cys   Phe   Ser
          -20                           -15                           -10

Thr   Thr   Ala   Leu   Ser   Arg   Ser   Tyr   Ser   Leu   Leu   Arg   Phe   Gln   Gln   Arg
          -5                      1                 5                                   10

Gln   Ser   Leu   Lys   Glu   Cys   Gln   Lys   Leu   Leu   Gly   Gln   Leu   Pro   Ser   Thr
                      15                      20                            25

Ser   Gln   His   Cys   Leu   Glu   Ala   Arg   Met   Asp   Phe   Gln   Met   Pro   Glu   Glu
                30                            35                      40

Met   Lys   Gln   Glu   Gln   Gln   Phe   Gln   Lys   Glu   Asp   Ala   Ile   Leu   Val   Met
          45                            50                      55

Tyr   Glu   Val   Leu   Gln   His   Ile   Phe   Gly   Ile   Leu   Thr   Arg   Asp   Phe   Ser
    60                            65                      70                                  75

Ser   Thr   Gly   Trp   Ser   Glu   Thr   Ile   Ile   Glu   Asp   Leu   Leu   Lys   Glu   Leu
                      80                            85                                  90

Tyr   Trp   Gln   Met   Asn   Arg   Leu   Gln   Pro   Ile   Gln   Lys   Glu   Ile   Met   Gln
                      95                            100                           105

Lys   Gln   Asn   Ser   Thr   Thr   Glu   Asp   Thr   Ile   Val   Pro   His   Leu   Gly   Lys
                      110                           115                           120

Tyr   Tyr   Phe   Asn   Leu   Met   Gln   Tyr   Leu   Glu   Ser   Lys   Glu   Tyr   Asp   Arg
          125                           130                     135

Cys   Ala   Trp   Thr   Val   Val   Gln   Val   Gln   Ile   Leu   Thr   Asn   Val   Ser   Phe
    140                     145                           150                                 155

Leu   Met   Arg   Leu   Thr   Gly   Tyr   Val   Arg   Asp
                            160                     165
```

( 2 ) INFORMATION FOR SEQ ID NO:25:

( i ) SEQUENCE CHARACTERISTICS:
        ( A ) LENGTH: 186 amino acids
        ( B ) TYPE: amino acid
        ( D ) TOPOLOGY: unknown ( i i ) MOLECULE TYPE: protein ( i x ) FEATURE:
        ( A ) NAME/KEY: Protein
        ( B ) LOCATION: 22..186
        ( D ) OTHER INFORMATION: /note= "Bo-IFN-beta-2"

( x i ) SEQUENCE DESCRIPTION: SEQ ID NO:25:

| Met | Thr | His | Arg | Cys | Leu | Leu | Gln | Met | Val | Leu | Leu | Leu | Cys | Phe | Ser |
|---|---|---|---|---|---|---|---|---|---|---|---|---|---|---|---|
| -20 | | | | | | -15 | | | | | -10 | | | | |

| Thr | Thr | Ala | Leu | Ser | Arg | Ser | Tyr | Ser | Leu | Leu | Arg | Phe | Gln | Gln | Arg |
|---|---|---|---|---|---|---|---|---|---|---|---|---|---|---|---|
| -5 | | | | | 1 | | | | 5 | | | | | 10 | |

| Arg | Ser | Leu | Ala | Leu | Cys | Gln | Lys | Leu | Leu | Arg | Gln | Leu | Pro | Ser | Thr |
|---|---|---|---|---|---|---|---|---|---|---|---|---|---|---|---|
| | | | 15 | | | | | 20 | | | | | 25 | | |

| Pro | Gln | His | Cys | Leu | Glu | Ala | Arg | Met | Asp | Phe | Gln | Met | Pro | Glu | Glu |
|---|---|---|---|---|---|---|---|---|---|---|---|---|---|---|---|
| | | 30 | | | | | 35 | | | | | 40 | | | |

| Met | Lys | Gln | Ala | Gln | Gln | Phe | Gln | Lys | Glu | Asp | Ala | Ile | Leu | Val | Ile |
|---|---|---|---|---|---|---|---|---|---|---|---|---|---|---|---|
| | 45 | | | | 50 | | | | | 55 | | | | | |

| Tyr | Glu | Met | Leu | Gln | Gln | Ile | Phe | Asn | Ile | Leu | Thr | Arg | Asp | Phe | Ser |
|---|---|---|---|---|---|---|---|---|---|---|---|---|---|---|---|
| 60 | | | | | 65 | | | | | 70 | | | | | 75 |

| Ser | Thr | Gly | Trp | Ser | Glu | Thr | Ile | Ile | Glu | Asp | Leu | Leu | Glu | Glu | Leu |
|---|---|---|---|---|---|---|---|---|---|---|---|---|---|---|---|
| | | | | 80 | | | | | 85 | | | | | 90 | |

| Tyr | Glu | Gln | Met | Asn | His | Leu | Glu | Pro | Ile | Gln | Lys | Glu | Ile | Met | Gln |
|---|---|---|---|---|---|---|---|---|---|---|---|---|---|---|---|
| | | | 95 | | | | | 100 | | | | | 105 | | |

| Lys | Gln | Asn | Ser | Thr | Met | Gly | Asp | Thr | Thr | Val | Leu | His | Leu | Arg | Lys |
|---|---|---|---|---|---|---|---|---|---|---|---|---|---|---|---|
| | | 110 | | | | | 115 | | | | | 120 | | | |

| Tyr | Tyr | Phe | Asn | Leu | Val | Gln | Tyr | Leu | Lys | Ser | Lys | Glu | Tyr | Asn | Arg |
|---|---|---|---|---|---|---|---|---|---|---|---|---|---|---|---|
| | 125 | | | | | 130 | | | | | 135 | | | | |

| Cys | Ala | Trp | Thr | Val | Val | Arg | Val | Gln | Ile | Leu | Arg | Asn | Phe | Ser | Phe |
|---|---|---|---|---|---|---|---|---|---|---|---|---|---|---|---|
| 140 | | | | | 145 | | | | | 150 | | | | | 155 |

| Leu | Thr | Arg | Leu | Thr | Gly | Tyr | Leu | Arg | Glu |
|---|---|---|---|---|---|---|---|---|---|
| | | | | 160 | | | | | 165 |

(2) INFORMATION FOR SEQ ID NO:26:

(i) SEQUENCE CHARACTERISTICS:
 (A) LENGTH: 186 amino acids
 (B) TYPE: amino acid
 (D) TOPOLOGY: unknown (ii) MOLECULE TYPE: protein (ix) FEATURE:
 (A) NAME/KEY: Protein
 (B) LOCATION: 22..186
 (D) OTHER INFORMATION: /note= "Bo-IFN-beta-3"

(xi) SEQUENCE DESCRIPTION: SEQ ID NO:26:

| Met | Thr | Tyr | Arg | Cys | Leu | Leu | Pro | Met | Val | Leu | Leu | Leu | Cys | Phe | Ser |
|---|---|---|---|---|---|---|---|---|---|---|---|---|---|---|---|
| -20 | | | | | | -15 | | | | | -10 | | | | |

| Thr | Thr | Ala | Leu | Ser | Arg | Ser | Tyr | Ser | Leu | Leu | Arg | Phe | Gln | Gln | Arg |
|---|---|---|---|---|---|---|---|---|---|---|---|---|---|---|---|
| -5 | | | | | 1 | | | | 5 | | | | | 10 | |

| Arg | Ser | Ala | Glu | Val | Cys | Gln | Lys | Leu | Leu | Gly | Gln | Leu | His | Ser | Thr |
|---|---|---|---|---|---|---|---|---|---|---|---|---|---|---|---|
| | | | 15 | | | | | 20 | | | | | 25 | | |

| Pro | Gln | His | Cys | Leu | Glu | Ala | Lys | Met | Asp | Phe | Gln | Val | Pro | Glu | Glu |
|---|---|---|---|---|---|---|---|---|---|---|---|---|---|---|---|
| | | 30 | | | | | 35 | | | | | 40 | | | |

| Met | Asn | Gln | Ala | Gln | Gln | Phe | Arg | Lys | Glu | Asp | Ala | Ile | Leu | Val | Ile |
|---|---|---|---|---|---|---|---|---|---|---|---|---|---|---|---|
| | 45 | | | | 50 | | | | | 55 | | | | | |

| Tyr | Glu | Met | Leu | Gln | Gln | Ile | Phe | Asn | Ile | Leu | Thr | Arg | Asp | Phe | Ser |
|---|---|---|---|---|---|---|---|---|---|---|---|---|---|---|---|
| 60 | | | | | 65 | | | | | 70 | | | | | 75 |

| Ser | Thr | Gly | Trp | Ser | Glu | Thr | Ile | Ile | Glu | Asp | Leu | Leu | Val | Glu | Leu |
|---|---|---|---|---|---|---|---|---|---|---|---|---|---|---|---|
| | | | | 80 | | | | | 85 | | | | | 90 | |

| Tyr | Gly | Gln | Met | Asn | Arg | Leu | Gln | Pro | Ile | Gln | Lys | Glu | Ile | Met | Gln |
|---|---|---|---|---|---|---|---|---|---|---|---|---|---|---|---|
| | | | 95 | | | | | 100 | | | | | 105 | | |

| Glu | Gln | Asn | Phe | Thr | Met | Gly | Asp | Thr | Thr | Val | Leu | His | Leu | Lys | Lys |
|---|---|---|---|---|---|---|---|---|---|---|---|---|---|---|---|
| | | 110 | | | | | 115 | | | | | 120 | | | |

| | | | | | | | | | | | | | |
|---|---|---|---|---|---|---|---|---|---|---|---|---|---|
| Tyr | Tyr 125 | Phe | Asn | Leu | Val | Gln 130 | Tyr | Leu | Glu | Ser | Lys 135 | Glu | Tyr | Asn | Arg |
| Cys 140 | Ala | Trp | Thr | Val | Val 145 | Arg | Val | Gln | Ile | Leu 150 | Thr | Asn | Phe | Ser | Phe 155 |
| Leu | Met | Arg | Leu | Thr 160 | Ala | Ser | Leu | Arg | Asp 165 | | | | |

METHOD FOR TREATING TYPE 1 DIABETES USING α-INTERFERON AND/OR β-INTERFERON

BACKGROUND OF THE INVENTION

1. Field of the Invention

The present invention relates to a method of preventing or treating autoimmune diseases using a single subtype of α-interferon, β-interferon or mixtures, including hybrids and/or analogs thereof.

2. Description of the Background

The term "autoimmune disease" encompasses a wide variety of diseases. For example, the following diseases and conditions are examples of autoimmune diseases: Type 1 diabetes mellitus, rheumatoid arthritis, systemic lupus erythematosus, scleroderma, Sjogren's syndrome, mixed connective tissue disease, ankylosis spondylitis, Reiter's syndrome, psoriatic arthritis, hypersensitivity vasculitis, ulcerative colitis, cirrhosis, autoimmune uveitis, myasthenia gravis, Buerger's disease, Kawasaki's disease, systemic necrotizing vasculitis, regional enteritis and hypoparathyroidism. At present, many of these diseases are neither preventable nor curable.

While studies have been made in an attempt to reverse the disease process for some of these diseases, beneficial results inhibiting these autoimmune diseases are usually only transient at best and are obtained with significant drug toxicity. For example, in attempting to treat or reverse the disease process for patients having Type 1 diabetes mellitus with cyclosporin A, biopsy-proven nephrotoxic effects were observed in some patients after only one year of treatment. Unfortunately, more than one year of treatment appears to be necessary.

Moreover, recurrent autoimmune disease may occur in transplanted tissue and can be an important cause of transplant failure. For example, all patients with Type 1 diabetes mellitus receiving transplanted islet cells suffer from rejection thereof due, in part, to recurrent autoimmune disease.

Hence, a need exists for a method by which recurrent autoimmune disease could be prevented, and by which autoimmune diseases may be prevented and/or treated.

SUMMARY OF THE INVENTION

Accordingly, the present invention provides a method of preventing and/or treating autoimmune disorders by administering to a mammal, a single subtype of α-interferon, β-interferon or hybrids and/or analogs or mixtures thereof.

The present invention also provides a method of treating early asymptomatic stages of autoimmune disease in a mammal, which entails administering to a mammal, a single subtype of α-interferon, β-interferon or hybrids, analogs or mixtures thereof.

The above objects and other objects are provided by a method of preventing or treating an autoimmune disorder in a mammal or recurrent autoimmune disease in transplanted tissues or cells, which entails administering to a mammal an effective amount of a single subtype of α-interferon, β-interferon or a mixture thereof, including hybrids and/or analogs or mixture thereof.

DETAILED DESCRIPTION OF THE PREFERRED EMBODIMENTS

Figure 1:
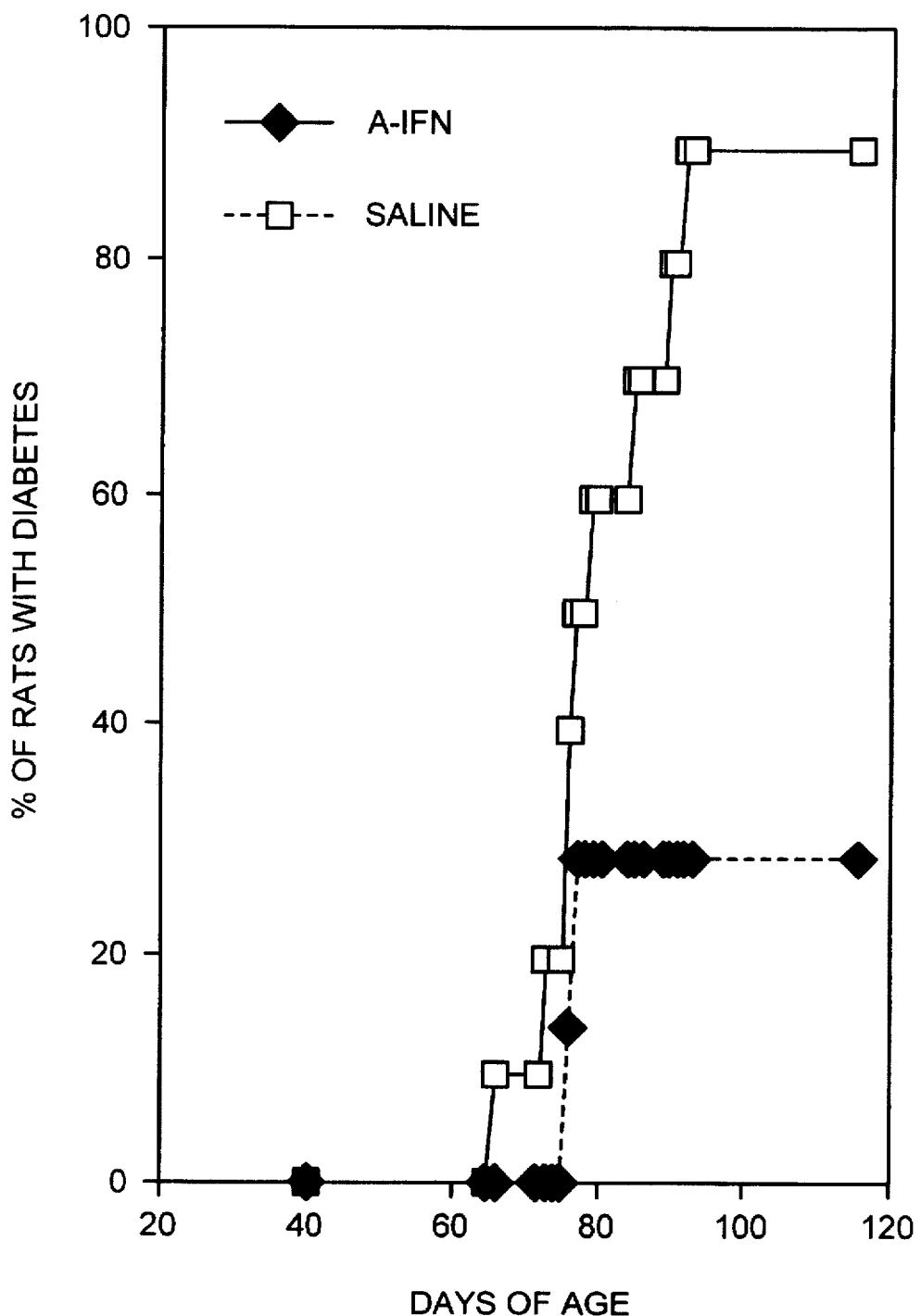
FIG. 1 compares the development of diabetes mellitus in diabetes prone biobreeding (DP-BB) rats treated with α-IFN (400,000 units per dose) versus saline (control).

For purposes of the present invention, the term "autoimmune disorder" means any disease or condition which is caused by or triggered by a breakdown of tolerance to autologous constituents, such as Type I diabetes mellitus, rheumatoid arthritis, systemic lupus erythematosus, scleroderma, Sjogren's syndrome, mixed connective tissue disease, ankylosis spondylitis, Reiter's syndrome, psoriatic arthritis, hypersensitivity vasculitis, ulcerative colitis, cirrhosis, autoimmune uveitis, myasthenia gravis, Buerger's disease, Kawasaki's disease, systemic necrotizing vasculitis, regional enteritis and hypoparathyroidism.

In accordance with the present invention, it has been surprisingly discovered that single subtypes of α- and/or β-interferon or mixtures thereof, including hybrids and/or analogs or mixtures thereof, can be used with great advantage in preventing or treating autoimmune disorders.

It has also been discovered, in accordance with the present invention, that the same single subtypes of α- and/or β-interferon or mixtures thereof, including hybrids and/or analogs or mixtures thereof may be used to advantage in treating asymptomatic conditions which are present prior to the clinically apparent onset of autoimmune disease, or in treating recurrent autoimmune disease, such as Type I diabetes mellitus in transplanted pancreas or islet tissue.

In accordance with the present invention, the single α- and/or β-interferon subtype used may be a purified, naturally occurring or recombinant subtype, or it may be a hybrid of two or more subtypes or an analog thereof. Further, mixtures containing any two or more of the above may be used in accordance with the present invention.

In accordance with the present invention, many variations of the α-IFN and/or β-IFN subtypes, hybrids and/or analogs may be used. Furthermore, in accordance with the present invention, the α-IFN and/or β-IFN may originate from any mammalian species. Thus, for example, bovine β-IFN subtypes may be used in human therapy.

First, α-IFN and/or β-IFN subtypes may be used which have a length of 166 amino acid units, and which have at least 60% of the consensus sequence shown below in Tables 1 and 2, respectively. The remaining portion of the consensus sequence and any portion of or all of the non-consensus portions of any α-IFN or β-IFN may be substituted by any other amino acid, whether naturally occurring or not. By the term "non-consensus" portion or "non-consensus" amino acids is meant those amino acids which do not fall within the amino acids which are sequentially common to α-IFN and/or β-IFNs as shown in Table 1. Thus, for example, any α-IFN subtype from Table 1 and/or any β-IFN from Table 2 may be used as a starting model, and up to 40% of the consensus sequence may be substituted and up to 100% of the non-consensus sequence may be substituted by amino acids, such as, for example, glycine, alanine, valine, leucine, isoleucine, serine, threonine, cysteine, cystine, methionine, aspartic acid, glutamic acid, asparagine, glutamine, lysine, hydroxylysine, histidine, arginine, phenylalanine, tyrosine and tryptophan or even arnithine or citrulline.

Second, α-IFN and/or β-IFN subtypes, hybrids and/or analogs may be used which are less than 166 amino acid residues. In accordance with the present invention, the same rules will apply here as with the first variation above, except that the overall sequence length may be abbreviated to at least 70%, preferably at least 80% (132 or 133 units), and more preferably still to at least 90% (149 or 150 units).

Third, the α-IFN and/or β-IFN subtypes, hybrids and/or analogs or mixtures thereof of the present invention may be incorporated as an "active portion" into a larger polypeptide or protein of the formula:

$$\epsilon\text{-}\gamma\text{-}\omega$$

wherein γ is the "active portion" as defined above, and ε and ω each independently represent from 0 to up to about 10,000 amino acids as defined above, with the proviso that the polypeptide or protein has the active portion, γ, topologically available at the surface of the polypeptide or protein in the event that it is folded in a three-dimensional structure. The design of such structures, such that a particular portion is available at the surface of the structure is within the skill of one in the art.

Further, in all of the above, the term "analog" means any active portion or sequence described herein having at least 60% of the same amino acids in the same sequence as any sequence described in Table 1 or Table 2 hereinbelow.

Generally, the term "interferon" refers to a family of proteins that confer non-specific resistance to a broad range of viral infections, affect cell proliferation and modulate immune responses. Three major interferons, α-, β- and γ have been identified based upon antigenic and physicochemical properties, the nature of the inducer, and the cellular source from which they are derived. IFNs-α and -β, known collectively as Type I interferon, are structurally related, are stable at pH 2 and compete for the same cell surface receptor. IFN-γ, known as Type II interferon, is structurally unrelated to Type I IFNs and is acid labile and has a different cell surface receptor.

α-IFN, refers to a family of highly homologous proteins that inhibit viral replication and cellular proliferation and which modulate immune responses. α-IFN is produced by many cells in the body, including peripheral blood leukocytes or lymphobloistoid cells upon exposure to live or inactivated virus, double-stranded RNA or bacterial products. Moreover, there are multiple subtypes of α-IFN which contain 165–166 amino acids and which have molecular weights of about 18,000 to 20,000 daltons.

β-IFN is a cytokine having antiviral, antiproliferative and immunomodulatory activities. Generally, β-IFN is a glycoprotein containing 166 amino acids having a molecular weight of about 20,000 daltons.

Generally, in accordance with the present invention, the amount of single subtype of α-IFN or β-IFN, hybrids, analogs or mixtures thereof administered per dose either prior to or after onset of disease is about $1\times10^5$ units to about $75\times10^6$ units with administrations being given from once per day to once per week. However, amounts may be used which are less than $1\times10^5$ units, such as $5\times10^4$ units or lower, or which are more than $75\times10^6$ units, such as $10\times10^7$ units or higher. Of course, the precise amount used will vary, depending upon the judgment of the attending physician, considering such factors as the age, weight and condition of the patient. While any mammal may be treated, such as dogs, cats, cows, horses or poultry, it is particularly desirable that the mammal treated be human.

Furthermore, in accordance with the present invention, the single subtype of α- and/or β-interferon or hybrids and/or analogs or mixtures thereof may be administered by any means of administration, such as orally, intravenously, intramuscularly, intraperitoneally or subcutaneously.

Generally, in accordance with the present invention any single subtype of α-IFN or β-IFN, hybrids and/or analogs or mixtures thereof, such as the human (HuIFN-α) subtypes may be used. The polypeptides or proteins may be used in either purified natural form or recombinant natural or hybrid or analog forms or mixtures thereof. While it is generally preferred to use species specific subtypes, non-species specific subtypes may also be used.

The amino acid sequences of many different α-IFN subtypes, such as Hu-IFNα are known. The following exemplary list is only illustrative, and by no means limitative.

TABLE 1

The Amino Acid Sequences of Different Hu IFN-α Subtypes Derived From cDNA or Genomic DNA Sequences*

|  | S1 | S10 | S20 | S23 | 1 | 10 | 20 |
|---|---|---|---|---|---|---|---|
| IFN-α consensus (SEQ ID NO:1) | MALSFSLLMA | VLVLSYKSIC | SLG | CDLPQTHSLG | NRRALILLAQ |  |  |
| IFN-α1 (SEQ ID NO:2) | ..SP.A...V | LV...C..S. | ... | ...E....D | ...T.M.... |  |  |
| IFN-αD (SEQ ID NO:3) | ..SP.A...V | LV...C..S. | ... | ...E....D | ...T.M.... |  |  |
| IFN-α2 (SEQ ID NO:4) | ...T.A..V. | L....C..S. | .V. | .......... | S..T.M.... |  |  |
| IFN-αA (SEQ ID NO:5) | ...T.A..V. | L....C..S. | .V. | .......... | S..T.M.... |  |  |
| IFN-αK (α6)(SEQ ID NO:6) | ...P.A.... | LV...C..S. | .D | .......... | H..T.M.M... |  |  |
| IFN-α5 (G)(SEQ ID NO:7) | ...P.V.... | LV..NC.... | ... | .........S | ..T.M.M... |  |  |
| IFN-αH1 (αH2)(SEQ ID NO:8) | ...P...M.. | LV...C..S. | ... | .N.S.....N | ...T.M.M.. |  |  |
| IFN-αB2 (α8)(SEQ ID NO:9) | ...T.Y..V. | LV......FS | ... | .......... | .......... |  |  |
| IFN-αB (SEQ ID NO:10) | ...T.Y.MV. | LV......FS | ... | .......... | .......... |  |  |
| IFN-α4b (SEQ ID NO:11) | .......... | .......... | ... | .......... | .......... |  |  |
| IFN-αC (SEQ ID NO:12) | .......... | .......... | ... | .......... | .........G. |  |  |
| IFN-αL (βα10)(SEQ ID NO:13) | .......... | .........* | ... | .......T.R | .........G. |  |  |
| IFN-αJ1 (α7)(SEQ ID NO:14) | ..R......V | .......... | ... | .........R | .......... |  |  |
| IFN-αJ2 (SEQ ID NO:15) | ..R......V | .......... | ... | .........R | .......... |  |  |
| IFN-αf (SEQ ID NO:16) | .......... | .......... | ... | .......... | .......... |  |  |
| IFN-αF (SEQ ID NO:17) | .......... | .......... | ... | .......... | .......... |  |  |
| IFN-αWA (SEQ ID NO:18) | .......... | .......... | ... | .......... | .......... |  |  |
| IFN-αGk-1 (SEQ ID NO:19) | ...P...M.. | LV...C..S. | ... | .N.S.....N | ...T.M.L.. |  |  |
| IFN-α76 (SEQ ID NO:20) | .......... | .......... | ... | .......... | .......... |  |  |

TABLE 1-continued

The Amino Acid Sequences of Different Hu IFN-α
Subtypes Derived From cDNA or Genomic DNA Sequences*

|  | 30 | 40 | 50 | 60 | 70 |
|---|---|---|---|---|---|
| IFN-α consensus (SEQ ID NO:1) | MGRISPFSCL | KORHDFGFPQ | EEFDGNQFQK | AQAISVLHEM | IQQTFNLFST |
| IFN-α1 (SEQ ID NO:2) | .S....S... | M......... |  | .P.....L | ..I...T. |
| IFN-αD (SEQ ID NO:3) | .S....S... | M......... |  | .P.....L | ..I...T. |
| IFN-α2 (SEQ ID NO:4) | .R...L.... |  |  | .ET.P.... | ..I...... |
| IFN-αA (SEQ ID NO:5) | .RK..L.... |  |  | .ET.P.... | ..I...... |
| IFN-αK (α6)(SEQ ID NO:6) | .R...L.... | ......R... |  | .E......V |  |
| IFN-α5 (G)(SEQ ID NO:7) |  |  |  |  |  |
| IFN-αH1 (αH2)(SEQ ID NO:8) | .R........ | ......E... |  |  | M......... |
| IFN-αB2 (α8)(SEQ ID NO:9) | .R........ | ......E... | ...DK.... |  |  |
| IFN-αB (SEQ ID NO:10) | .R........ | ......E... | ...DK.... |  |  |
| IFN-α4b (SEQ ID NO:11) | ....H.... | ........E | ....H.... | T......... |  |
| IFN-αC (SEQ ID NO:12) |  | ......RI.. |  |  |  |
| IFN-αL (βα10)(SEQ ID NO:13) |  | ......RI.. |  |  |  |
| IFN-αJ1 (α7)(SEQ ID NO:14) |  | ....E.R..E | ....H.... | T......... |  |
| IFN-αJ2 (SEQ ID NO:15) |  | ...E.R..E | ....H.... | T......... |  |
| IFN-αf (SEQ ID NO:16) |  | ...P..L.. |  | T......... |  |
| IFN-αF (SEQ ID NO:17) |  |  |  |  |  |
| IFN-αWA (SEQ ID NO:18) | .....H.... | ....Y...... | .V........ | .....AF... |  |
| IFN-αGk-1 (SEQ ID NO:19) |  |  |  |  |  |
| IFN-α76 (SEQ ID NO:20) | ....H.... | .........E | ....H.... |  |  |

|  | 80 | 90 | 100 | 110 |
|---|---|---|---|---|
| IFN-α consensus (SEQ ID NO:1) | KDSSAAWDES | LLEKFSTELY | QQLNDLEACV | JQEVGVEETP |
| IFN-α1 (SEQ ID NO:2) | .........D | ..D..C.... |  | M..ER.G... |
| IFN-αD (SEQ ID NO:3) | .........D | ..D..C.... |  | M..ER.G... |
| IFN-α2 (SEQ ID NO:4) | .........T | ..D..Y.... |  | ..G...T... |
| IFN-αA (SEQ ID NO:5) | .........T | ..D..Y.... |  | ..G...T... |
| IFN-αK(α6) (SEQ ID NO:6) | ....V....R | ..D.I.Y.... |  | M...W.GG.. |
| IFN-α5(G) (SEQ ID NO:7) | ....T...T | ..D..Y.... | .........M | M......D.. |
| IFN-αH1 (αH2) (SEQ ID NO:8) | .N.......T | .....YI.F | .M........ |  |
| IFN-αB2 (α8) (SEQ ID NO:9) | ......L..T | ..DE.YI..D | .........S.. | M.....I.S. |
| IFN-αB (SEQ ID NO:10) | ......L..T | ..DE.YI..D | ........VLC | D.....I.S. |
| IFN-α4b (SEQ ID NO:11) | E......EQ. |  |  |  |
| IFN-αC (SEQ ID NO:12) | E......EQ. |  |  |  |
| IFN-αL (βα10) (SEQ ID NO:13) | E......EQ. | ........L |  |  |
| IFN-αJ1 (α7) (SEQ ID NO:14) | E......EQ. |  |  |  |
| IFN-αJ2 (SEQ ID NO:15) | E......EQ. |  |  |  |
| IFN-αd (SEQ ID NO:16) | E......EQ. |  | ....N..... | .....M.... |
| IFN-αF (SEQ ID NO:17) | .....T.EQ. | .........N | .....M.... |  |
| IFN-αWA (SEQ ID NO:18) | .........T | ..D..YI.F |  | T......IA |
| IFN-αGX-1 (SEQ ID NO:19) | .....T...T | ..D..Y.... | .........M | M......D.. |
| IFN-α76 (SEQ ID NO:20) | E......EQ. |  |  |  |

|  | 120 | 130 | 140 | 150 | 160 | 166 |
|---|---|---|---|---|---|---|
| IFN-α consensus (SEQ ID NO:1) | LMNEDSILAV | RKYFQRITLY | LTEKKYSPCA | WEVVRAEIMR | SFSFSTNLQK | RLRRKD |
| IFN-α1 (SEQ ID NO:2) | ...A...... | K...R..... |  |  | .LL....E | ....E |
| IFN-αD (SEQ ID NO:3) | ...V...... | K...R..... |  |  | .LL....E | ....E |
| IFN-α2 (SEQ ID NO:4) | ..K....... |  | .K........ |  | ..L....E | S..S.E |
| IFN-αA (SEQ ID NO:5) | ..K....... |  | .K........ |  | ..L....E | S..S.E |
| IFN-αK (α6) (SEQ ID NO:6) |  |  |  |  | ...S.R..E | ....E |
| IFN-α5(G) (SEQ ID NO:7) | ...V....T. |  |  |  | ..L.A..E | ....E |
| IFN-αH1 (αH2) (SEQ ID NO:8) |  | K......... | M......... |  |  | ...... |
| IFN-αB2 (α8) (SEQ ID NO:9) | ..Y....... |  | ........S.. |  | ..L.I.... | ..KS.E |
| IFN-αB (SEQ ID NO:10) | ..Y....... |  | ........S.. |  | ..L.I.... | ..KS.E |
| IFN-α4b (SEQ ID NO:11) | ...V...... |  |  |  | .L........ | ...... |
| IFN-αC (SEQ ID NO:12) |  |  | .I.R...... |  | .L........ | ...... |
| IFN-αL (βα10) (SEQ ID NO:13) |  |  | .I.R...... |  | .L........ | ...... |
| IFN-αJ1 (α7) (SEQ ID NO:14) | ....F.... |  | .M........ |  | .........K. | G..... |
| IFN-αJ2 (SEQ ID NO:15) | ....F.... |  | .M........ |  |  | ...... |
| IFN-αd (SEQ ID NO:16) |  |  |  |  | .L........ | I..... |
| IFN-αF (SEQ ID NO:17) | ...V...... | K......... |  |  | ..L.KIF.E | ....E |
| IFN-αWA (SEQ ID NO:18) |  |  | .MG....... |  |  | G..... |
| IFN-αGX-1 (SEQ ID NO:19) | ...V....T. |  |  |  | ..L.A..E | ....E |
| IFN-α76 (SEQ ID NO:20) |  |  |  |  | .L........ | ...... |

*The sequences, including the signal peptide, are presented in comparison with a consensus sequence, and residues are indicated only when they are different from the consensus sequence. In the latter, residues common to all listed sequences are underlined. Sequences with numeric designation are from Weissmann and collaborators, and sequences A to L are from Pestka, Goeddel et al. The Table utilizes standard one-letter amino acid symbols.

TABLE 2

Comparison of the Deduced Amino Acid Sequences,
Including the Signal Peptides,
of IFNβ of Human, Murine, and Bovine Origin.*

|  | S10 | S20 | S21 |
|---|---|---|---|
| IFN-β consensus (SEQ ID NO:21) | MTXRCLLQXA | LLLCFSTTAL | S |
| Hu-IFN-β (SEQ ID NO:22) | ..NK....I. | .......... | . |
| Mu-IFN-β (SEQ ID NO:23) | .NN.WI.HA. | F......... | . |
| Bo-IFN-β₁ (SEQ ID NO:24) | ..Y.....MV | .......... | . |
| Bo-IFN-β₂ (SEQ ID NO:25) | ..H.....MV | .......... | . |
| Bo-IFN-β₃ (SEQ ID NO:26) | ..Y....PMV | .......... | . |

|  | 10 | 20 | 30 |
|---|---|---|---|
| IFN-β consensus (SEQ ID NO:21) | XSYXLLXFQQ | RXSXXXCQKL | LXQLXXXXXX |
| Hu-IFN-β (SEQ ID NO:22) | M..N..G.L. | .S.NFQ.... | .W..NGRLEY |
| Mu-IFN-β (SEQ ID NO:23) | IN.KQ.QL.E | .TNIRK..E. | .E..NGKI.. |
| Bo-IFN-β₁ (SEQ ID NO:24) | R..S..R... | .Q.LKE.... | .G..PSTSQH |
| Bo-IFN-β₂ (SEQ ID NO:25) | R..S..R... | .R.LAL.... | .R..PSTPQH |
| Bo-IFN-β₃ (SEQ ID NO:26) | R..S..R... | .R.AEV.... | G..HSTPQH |

|  | 40 | 50 | 60 |
|---|---|---|---|
| IFN-β consensus (SEQ ID NO:21) | CLXXRMDFXX | PEEMKQXQQF | QKEDAALXIY |
| Hu-IFN-β (SEQ ID NO:22) | ..KD..N.DI | ...I.L.... | ......T.. |
| Mu-IFN-β (SEQ ID NO:23) | N.TY.A..KI | ....TE.KM. | ..SYT.FA.Q |
| Bo-IFN-β₁ (SEQ ID NO:24) | .EA....QM | ......E... | ....I.VM. |
| Bo-IFN-β₂ (SEQ ID NO:25) | .EA....QM | ......A... | ....I.V.. |
| Bo-IFN-β₃ (SEQ ID NO:26) | .EAK...QV | ....N.A... | R....I.V.. |

|  | 70 | 80 | 90 |
|---|---|---|---|
| IFN-β consensus (SEQ ID NO:21) | EMLQNIFXIF | PXDFSSTGWN | ETIVEXLLXE |
| Hu-IFN-β (SEQ ID NO:22) | .......A.. | .Q.S....... | .....N..AN |
| Mu-IFN-β (SEQ ID NO:23) | .....V.LV. | .NN........ | ....VR..D. |
| Bo-IFN-β₁ (SEQ ID NO:24) | .V..H..G.L | TR........S | ...LD..K. |
| Bo-IFN-β₂ (SEQ ID NO:25) | ....Q..N.L | TR........S | ...LD..E. |
| Bo-IFN-β₃ (SEQ ID NO:26) | ....Q..N.L | TR........S | ...LD..V. |

|  | 100 | 110 | 120 |
|---|---|---|---|
| IFN-β consensus (SEQ ID NO:21) | LYXQXNXLKT | VLEEKXEKEN | XTXGXXMSS——L |
| Hu-IFN-β (SEQ ID NO:22) | V.B.I.H... | ....L...D | F.R.KL...——. |
| Mu-IFN-β (SEQ ID NO:23) | .HQ.TVF... | .....Q.—.R | L.WE———...TA. |
| Bo-IFN-β₁ (SEQ ID NO:24) | ..W.M.R.QP | IQK.IMQ.Q. | S.TEDTIV———P |
| Bo-IFN-β₂ (SEQ ID NO:25) | ..E.M.H.EP | IQK.IMQ.Q. | S.M.DTTV———. |
| Bo-IFN-β₃ (SEQ ID NO:26) | ..G.M.R.QP | IQK.IMQEQ. | F.M.DTTV———. |

|  | 130 | 140 | 150 |
|---|---|---|---|
| IFN-β consensus (SEQ ID NO:21) | HLKXYYXRXX | XYLKXKEYXX | CAWTVVRVEI |
| Hu-IFN-β (SEQ ID NO:22) | ...R..G.IL | H...A...SH | ....I..... |
| Mu-IFN-β (SEQ ID NO:23) | ...S...W.VQ | R...LMK.NS | Y..M...A.. |
| Bo-IFN-β₁ (SEQ ID NO:24) | ..GK..FNLM | Q..ES...DR | ........Q.Q. |
| Bo-IFN-β₂ (SEQ ID NO:25) | ..RK..FNLV | Q...S...NR | ........Q. |
| Bo-IFN-β₃ (SEQ ID NO:26) | ...K..FNLV | Q..ES...NR | ........Q. |

|  | 160 | 166 |
|---|---|---|
| IFN-β consensus (SEQ ID NO:21) | LRNFXFIXRL | TGYLRN |
| Hu-IFN-β (SEQ ID NO:22) | ....Y..N.. | ....... |
| Mu-IFN-β (SEQ ID NO:23) | F...LI.R.. | .RNFQ. |
| Bo-IFN-β₁ (SEQ ID NO:24) | .T.VS.I.M. | ...V.D |
| Bo-IFN-β₂ (SEQ ID NO:25) | ....S.I.T.. | ....E |
| Bo-IFN-β₃ (SEQ ID NO:26) | .T..S.I.M.. | .AS..D |

*The sequences are presented as they differ from a consensus sequence, and the amino acids of the consensus sequence that are common to all sequences are underlined. Positions where no clear consensus exists are indicated in the consensus sequence by "X". The table is adapted from Pestka using the standard one-letter amino acid code.

Table 1 provides a detailed sequence listing of various α-interferon subtypes, showing a consensus sequence for all. By "consensus sequence" is meant that sequence which is common to all α-IFN and β-IFN subtypes. See Tables 1 and 2. In accordance with the present invention, any α-interferon subtype may be used singly or in admixture with others or as hybrids and/or analogs or mixtures thereof as long as it contains, at the least, 60% of the consensus sequence shown in Table 1 as described above or a sequence which exhibits substantially the same α-IFN activity against autoimmune disease as a sequence having at least that portion of the consensus sequence.

Table 2 provides a comparison of detailed sequence listings for β-interferon of human, murine and bovine origin. In accordance with the present invention, any β-interferon subtype may be used as long as it contains at least 60% of the consensus sequence shown in Table 2 as described above or a sequence which exhibits substantially the same β-IFN activity against autoimmune disease as a sequence having at least the consensus sequence.

In both Tables, the standard one-letter amino acid formulas are used. See Barker, *Organic Chemistry of Biological Compounds*, (Prentice Hall).

Generally, the phrase "substantially the same IFN activity" means an autoimmune process or disease inhibitory activity which may be anywhere from in excess of 1% to up to about 1000% of the same activity of a sequence having, at least, about 60% of the consensus sequence of the sequences of Tables 1 or 2. Preferably, however, at least about 70%, and more preferably about 80% of the consensus sequence is present. It is most preferred, however, if at least about 90% of the consensus sequence, is present.

More preferably still, the other sequences are, in general, at least 95% or 100% homologous with those having, at least, the consensus sequence.

In the various subtypes of α-IFN and β-IFN, amino acid residues thereof may be substituted in the nonconsensus portion by other amine residues, such as, for example, glycine, alanine, valine, leucine, isoleucine, serine, threonine, cysteine, cystine, methionine, aspartic acid, glutamic acid, asparagine, glutamine, lysine, hydroxylysine, histidine, arginine, phenylalanine, tyrosine and tryptophan. However, these are only exemplary and other amino acids, such as ornithine or citrulline, for example, may also be used.

Further, hybrid interferons may be constructed and used, for example, from IFLrA and IFLrD interferon-coding sequences. If necessary, purification may be effected using a known monoclonal antibody to human leukocyte interferon. Such hybrid interferons are well known as described Pestka et al, *Journal of Biological Chemistry*, vol. 257, No. 19, Oct. 10, 1982, pp. 11497–11502.

However, any hybrid α-IFN and/or β-IFN may be used. For example, other hybrids such as IFLrA1-62/D64-166 (Bgl II), IFLrA1-91/D93-166 (PUU II), IFLrD1-92/A92-165 (PUU II), IFLrD1-63/A63-165 (Bgl II), or IFLrA1-62/D64-92/A92-165 (Bgl II-PUU II) may be used. These are only exemplary and others may be used.

Generally, analogs of the α-IFN and/or β-IFN or hybrid interferons or mixtures thereof described herein may also be used.

The present invention will now be further illustrated by reference to certain examples which are provided solely for purposes of illustration and are not intended to be limitative.

Studies were performed with diabetes prone-biobreeding (DP-BB) rats which constitute an acceptable model for Type 1 diabetes in humans.

EXAMPLE 1

This experiment was designed to determine if the administration of a hybrid α-interferon at a dose of 400,000 units can prevent the development of diabetes. See FIG. 1.

DP-BB rats were divided into two groups; one being α-IFN treated (n=7) and the other being saline treated (control) (n=10).

rHu IFN-alpha-A/D Bgl II (Hoffmann La Roche) was administered at a dose of 400,000 units intraperitoneally three times a week beginning at approximately 40 days of age for about 8 weeks. Animals were diagnosed with diabetes when blood glucoses on two consecutive days exceeded 200 mg %. Animals were sacrificed at diagnosis of diabetes or at 120–130 days in the case of non-diabetic animals.

Using the survival curve analysis of Meier et al, the development of diabetes in the animals in the α-IFN-treated group was significantly lower than that for animals in the saline group (p<0.001).

EXAMPLE 2

This experiment was designed to determine if the administration of a lower amount of the same α-interferon as used in Example 1 to DP-BB rats can alter the development of diabetes and insulitis.

Data from the treatment groups from two identically performed experiments are combined and described. (See FIG. 2) DP-BB rats were divided into the following treatment groups: Group 1: normal saline (n=17); Group 2: α-IFN (35–40) day (n=15); and Group 3:α-IFN(28–30) day (n=6). Animals in the appropriate groups were administered (rHuIFN-alpha A/D Bgl II) 100,000 units intraperitoneally three times a week beginning at "35–40" days of age in Group II and "28–30" days of age in Group III. Treatment was discontinued after 6 weeks in the α-IFN(35–40) day group and continued until sacrifice in the α-IFN(28–30) day group.

Using the survival curve analysis of Meier et al, the development of diabetes in the animals in the α-IFN-(35–40) day and A-IFN-(28–30) day groups were significantly slower than that for animals in the saline control group (p<0.001). Thus, it is concluded that α-IFN administration at a dose of 100,000 units per injection prevents the development of diabetes in DP BB rats. It is noted that treatment was continued for six weeks in Group 2, but the effect thereof was long lasting and continued to the end of the experiment which was more than forty (40) days later.

Figure 2:
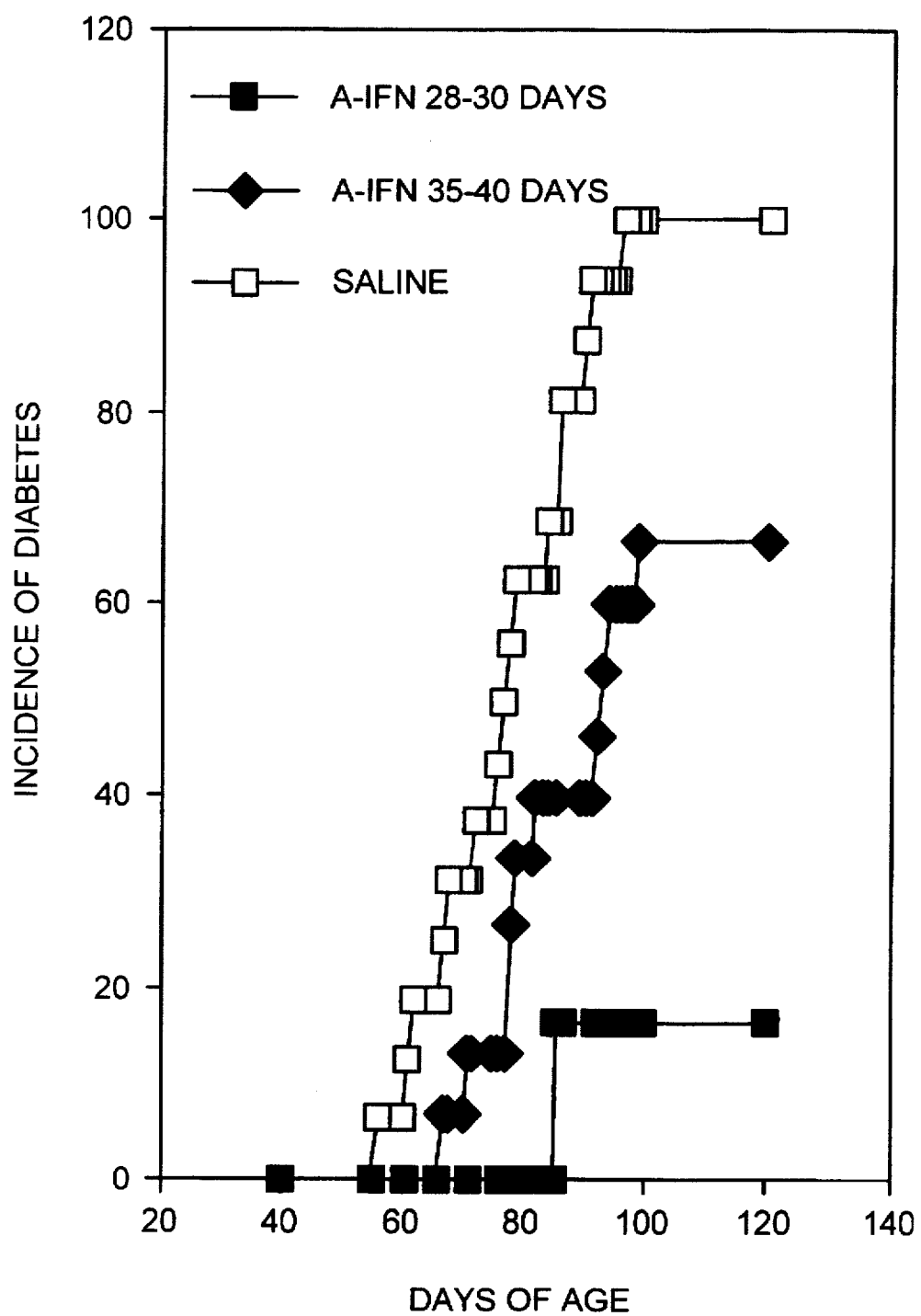
FIG. 2 illustrates the effect of α-IFN (at 100,000 units/dose) treatment on the development of diabetes mellitus in DP-BB rats.

FIG. 2 also shows that doses of α-IFN lower than 400,000 units may be used to reduce the incidence of diabetes mellitus. For example, a dose of as low as about 100,000 units may be used effectively.

EFFECT OF A-IFN ADMINISTRATION ON PANCREATIC HISTOPATHOLOGY

Histopathologic examination of the pancreas revealed a decrease in the amount of mononuclear infiltration within the islet in animals treated with α-IFN than with saline. Thus, α-IFN administration appears to reduce the inflammatory response within the islet rather than inhibiting the islet destructive activity of immune cells within the islets.

As noted above, the present invention may be used to treat clinically apparent autoimmune disease, asymptomatic states which exist prior to clinically apparent autoimmune disease, and even "pre-states" or "pre-conditions" which exists in the mammalian body prior to the onset of the symptomatic states. These conditions may include risk factors for autoimmune disease.

As used herein, the term "risk factor" includes genetic markers, other physiological markers, such as those mentioned above, and also a combination thereof.

For example, the present invention may be used to treat the pre-diabetic state, which may be detected in humans by any one or all of the following, for example: i) the presence of serum islet cell antibodies, ii) the presence of serum insulin antibodies and iii) a depressed first phase insulin response (release) to intravenous glucose injection. Thus, the same treatment regime may be used for the preliminary conditions prior to disease as for the disease, itself.

Thus, in accordance with the present invention, various genetic markers may be used to identify mammals, particularly humans, which or who are at risk for one or more autoimmune diseases. Such genetic markers or tests for the detection of such genetic markers are well known to those skilled in the art. In essence, if a mammalian host or patient tests positive or exhibits a given level of risk for one or more of these markers or factors, then depending upon the discretion of the treating physician or veterinarian, treatment may be commenced in accordance with the present invention.

Furthermore, the same treatment regimen as described above may be used in inhibiting recurrent autoimmune disease within transplanted tissue that contributes to graft failure. For example, α-IFN or β-IFN or the hybrids and/or analogs or mixtures thereof of the present invention may be used to advantage in inhibiting recurrent diabetes in the transplanted pancreas or islet cells in a patient having Type I diabetes. This is quite advantageous inasmuch as the conventional approach used in attempting to obtain such inhibition has entailed the administration of high doses of toxic drugs, such as cyclosporin A; steroids, such as prednisone; azathioprine, FK-506 and anti-leukocyte globulin, with only moderate success.

Thus, the present invention provides a method of treating asymptomatic conditions which precede onset of a clinically apparent autoimmune disease, which entails administering to a mammal presenting such symptoms and/or conditions an amount of a single subtype of α-interferon, β-interferon or a mixture, including hybrids, thereof effective to alleviate or reduce the symptoms and/or conditions.

Further, while each of the above methods may be practiced with any mammal, such as those noted previously, these methods are particularly advantageous with humans.

The present invention also provides pharmaceutical compositions which includes at least one active ingredient and one or more pharmaceutically acceptable excipients. Generally, the term "active ingredient" is intended to mean any one or more subtypes, hybrids and/or analogs or mixtures thereof of the present invention, either alone or in combination with each other, and optionally with any other active ingredient which may be used to treat autoimmune diseases.

Thus, for example, any one of the α-IFN subtypes recited in Table 1 may be used alone or in combination with each other or in combination with the human β-IFN of Table 2 as an active ingredient. Additionally, any hybrids and/or analogs or mixtures thereof may be so used. Thus, for example, IFN-α1 may be mixed with IFN-α GK-1 in combination with an excipient and optionally with a conventional medicament for treating autoimmune disease.

The pharmaceutical composition may, for example, take the form of suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatin and polyvinyl pyrrolidone; (c) moisturizing agents, e.g. glycerol; (d) disintegrating agents, e.g. agar—agar, calcium carbonate and sodium bicarbonate; (e) agents for retarding dissolution, e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; and (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain pacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the abovementioned diluents.

The diluents to be used in pharmaceutical compositions adapted to be formed into suppositories can, for example, be the usual water-soluble diluents, such as polyethylene glycols and fats (e.g. cocoa oil and high esters (e.g. $C_{14}$-alcohol with $C_{16}$-fatty acid)) or mixtures of these diluents.

The pharmaceutical compositions which are solutions and emulsions can, for example, contain the customary diluents, such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example, ground nut oil), glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminum metahydroxide, bentonite, agar—agar and tragacanth or mixtures thereof.

All the pharmaceutical compositions according to the invention can also contain coloring agents and preservatives as well as perfumes and flavoring additions (e.g. peppermint oil and eucalyptus oil) and sweetening agents (e.g. saccharin).

The pharmaceutical compositions according to the invention generally contain from 0.5% to 90% of one or both the active ingredient by weight of the total composition.

In addition to a compound of the invention, the pharmaceutical compositions and medicaments according to the invention can also contain other pharmaceutically active compounds.

Any diluent in the medicaments of the present invention may be any of those mentioned above in relation to the pharmaceutical compositions of the present invention. Such medicaments may include well known pharmaceutically acceptable solvents generally having a molecular weight of less than about 200 as the single diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The production of the above-mentioned pharmaceutical compositions and medicaments may be carried out by any method known in the art, for example, by mixing the active ingredient(s) with the diluent(s) to form a pharmaceutical composition (e.g. a granulate) and then forming the composition into the medicament (e.g. tablets).

For pharmaceutical compositions intended for oral administration, the same may be coated using coating materials which are well known in the art. The amount of coating composition to be applied is generally such that not more than 4% of the drug must leach out into artificial saliva within a period of two minutes at 20°–40° C. Among the most popular coating materials are: hydroxypropylcellulose, methylhydroxypropylcellulose, polyethylene oxide and polyvinyl pyrrolidone. These water-soluble polymers can be used alone or in admixture with water-insoluble polymers, such as ethylcellulose, polyvinylacetate, methylacrylate/methyl methacrylate, cellulose acetate phthalate, cellulose acetate butyrate, cellulose acetate propionate, polyvinylidene chloride, zein, and certain waxes as long as the resulting film is water-permeable. In the preferred embodiment, the coating material is applied to the pharmaceutical composition to the extent of at least 15% by weight of the complex. This insures almost complete taste masking. Where coating is done with water-soluble, film-formers, there is no substantial change of drug availability experienced in the gastro-intestinal juices between coated and uncoated drug/resin particles.

Generally, the various α-IFN and/or β-IFN subtypes, hybrids, or analogs described above may be either purchased commercially or may be produced in accordance with well known fermentative methods, such as are disclosed in *Current Protocols in Molecular Biology* (Wiley 1987). Further, these subtypes, hybrids or analogs may be purchased from commercial entities, such as Roche Laboratories, Schering or Purdue Frederick, for example.

Moreover, the polypeptides of the present invention may be synthesized using a standard solid phase or liquid phase amino acid synthesis or may be synthesized in accordance with U.S. Pat. Nos. 4,058,512 and 4,235,772 both of which are incorporated herein in the entirety. Also, these polypeptides may be readily obtained by custom synthesis from a variety of commercially available chemical supply companies.

Further, as indicated above, these polypeptides may be prepared by the fermentation of transformed microorganisms containing a synthetic gene coding for the same. Conventional techniques may be used for the synthesis of the appropriate gene and for the transformation of a host microorganism. As a host microorganism, *E. coli*, for example, may be used.

Finally, as noted above, the present polypeptides, as widely described above, may be used advantageously in treating hypoparathyroidism in mammals, particularly, in humans. In this aspect of the present invention, the same amounts used and modes of administration may be used as described above.

Having now described the present invention it will be apparent to the artisan that many changes and modifications may be made to the above-described embodiments without departing from the spirit and the scope of the present invention.

What is claimed and desired to be secured by U.S. Letters Patent:

1. A method of treating Type 1 diabetes in a mammal, which method comprises administering to a mammal having Type 1 diabetes mellitus an effective amount of at least one naturally-occurring Type 1 interferon, a synthetic Type 1 interferon analog or a hybrid Type 1 interferon, wherein said Type 1 interferon analog or hybrid binds to the same receptor as a naturally occurring Type 1 interferon.

2. The method of claim 1, wherein said mammal is a human.

3. The method of claim 1, wherein an α- or β-interferon or a synthetic analog thereof is administered.

4. The method of claim 1, wherein said effective amount ranges from about $1\times10^5$ units to about $10\times10^7$ units for administration.

5. The method of claim 4, wherein the effective amount ranges from about $1\times10^6$ to about $75\times10^6$ units for administration.

6. The method of claim 1, wherein a naturally-occurring α-interferon or β-interferon, synthetic analog thereof, or hybrid α- or β-interferon is administered.

7. The method of claim 6, wherein a naturally-occurring α-interferon or β-interferon is administered.

8. The method of claim 1, wherein said hybrid Type I interferon is rHuIFNα-A/D Bgl II.

9. A method of treating an asymptomatic preclinical state of Type 1 diabetes mellitus in a mammal at risk of developing Type 1 diabetes mellitus, which comprises administering to said mammal an effective amount of at least one naturally occurring Type 1 interferon, a synthetic Type 1 interferon analog, or a hybrid Type 1 interferon wherein said Type 1 interferon analog or hybrid binds the same receptor as a naturally occurring Type 1 interferon.

10. The method of claim 9, wherein said mammal is a human.

11. A method of treating recurrent Type 1 diabetes mellitus in a mammal having recurrent Type 1 diabetes mellitus, comprising administering an effective amount of at least one naturally occurring Type 1 interferon, a synthetic Type 1 interferon analog, or a hybrid Type 1 interferon wherein said Type 1 interferon analog or hybrid binds the same receptor as a naturally occurring Type 1 interferon.

12. The method of claim 11, wherein said mammal is a human.

13. The method of claim 11, wherein the mammal which is treated comprises transplanted pancreatic or islet tissue.

14. The method of claim 13, wherein a naturally-occurring α- or β-interferon or a synthetic analog thereof is administered.

15. The method of claim 11, wherein said effective amount ranges from about $1\times10^5$ units to about $10\times10^7$ units per administration.

16. The method of claim 15, wherein said effective amount ranges from about $1\times10^6$ to about $75\times10^6$ units per administration.

17. The method of claim 11, wherein a naturally-occurring α-interferon or β-interferon or a synthetic, analog, or hybrid thereof is administered.

18. The method of claim 17, wherein a naturally-occurring α-interferon or β-interferon is administered.

19. The method of claim 11, wherein a naturally-occurring α-interferon or β-interferon, or a hybrid or synthetic analog thereof is administered.

20. A method of treating Type 1 diabetes in a mammal comprising administering to a mammal in need of such treatment a therapeutically effective amount of α-interferon.

21. A method of preventing Type 1 diabetes in a mammal comprising administering to a mammal at risk of developing Type 1 diabetes mellitus an effective amount of at least one naturally-occurring Type 1 interferon, a synthetic Type 1 interferon analog or a hybrid Type 1 interferon, wherein said Type 1 interferon analog or hybrid binds to the same receptor as a naturally occurring Type 1 interferon.

22. The method of claim 21, wherein a naturally-occurring α-interferon or β-interferon, or a hybrid or synthetic analog thereof is administered.

23. A method of preventing recurrent Type 1 diabetes mellitus in a mammal at risk of developing recurrent Type 1 diabetes mellitus comprising administering an effective amount of at least one naturally occurring Type 1 interferon, a synthetic Type interferon analog, or a hybrid Type 1 interferon, wherein said Type 1 interferon analog or hybrid binds the same receptor as a naturally occurring Type 1 interferon.

24. The method of claim 23, wherein a naturally-occurring α-interferon or β-interferon, or an analog thereof is administered.

* * * * *